US012691173B2

(12) United States Patent
Yin et al.

(10) Patent No.: US 12,691,173 B2
(45) **Date of Patent: *Jul. 28, 2026**

(54) TOLL-LIKE RECEPTOR AGONIST-NANOPARTICLE VACCINE ADJUVANT

(71) Applicant: The Board of Trustees of the Leland Stanford Junior University, Stanford, CA (US)

(72) Inventors: Qian Yin, Los Altos, CA (US); Mark M. Davis, Atherton, CA (US); Wei Luo, Redwood City, CA (US); Bali Pulendran, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 195 days.

This patent is subject to a terminal disclaimer.

(21) Appl. No.: 18/287,444

(22) PCT Filed: Apr. 20, 2022

(86) PCT No.: PCT/US2022/025497

§ 371 (c)(1),
(2) Date: Oct. 18, 2023

(87) PCT Pub. No.: WO2022/226035

PCT Pub. Date: Oct. 27, 2022

(65) Prior Publication Data

US 2024/0207394 A1 Jun. 27, 2024

Related U.S. Application Data

(60) Provisional application No. 63/177,709, filed on Apr. 21, 2021.

(51) Int. Cl.

| | |
|---|---|
| ***A61K 39/39*** | (2006.01) |
| ***A61K 39/00*** | (2006.01) |
| ***A61K 39/215*** | (2006.01) |
| ***A61K 47/59*** | (2017.01) |
| ***A61K 47/69*** | (2017.01) |
| ***A61P 37/04*** | (2006.01) |

(52) U.S. Cl.
CPC ............ *A61K 39/39* (2013.01); *A61K 39/215* (2013.01); *A61P 37/04* (2018.01); *A61K 2039/54* (2013.01); *A61K 2039/543* (2013.01); *A61K 2039/55511* (2013.01)

(58) Field of Classification Search
None
See application file for complete search history.

(56) References Cited

U.S. PATENT DOCUMENTS

| | | | | |
|---|---|---|---|---|
| 8,906,381 | B2 | 12/2014 | Iannacone | |
| 9,789,195 | B2 * | 10/2017 | Cheng | A61K 47/6857 |
| 2008/0131466 | A1 | 6/2008 | Reed et al. | |
| 2010/0233251 | A1 | 9/2010 | Von Andrian et al. | |
| 2010/0303850 | A1 * | 12/2010 | Lipford | A61P 43/00 424/193.1 |
| 2011/0223201 | A1 * | 9/2011 | Lipford | A61K 47/6935 424/193.1 |
| 2011/0293701 | A1 | 12/2011 | Bratzler et al. | |
| 2012/0087890 | A1 * | 4/2012 | Iannacone | A61K 39/00 424/85.4 |
| 2020/0164090 | A1 | 5/2020 | Yin et al. | |
| 2021/0023208 | A1 | 1/2021 | Seder et al. | |

FOREIGN PATENT DOCUMENTS

| | | |
|---|---|---|
| WO | WO2010042863 | 4/2010 |
| WO | WO2010138194 | 12/2010 |

OTHER PUBLICATIONS

Patinote, Cindy, et al. "Agonist and antagonist ligands of toll-like receptors 7 and 8: Ingenious tools for therapeutic purposes." European journal of medicinal chemistry 193 (2020): 112238. (Year: 2020).*
Tong, Rong, and Jianjun Cheng. "Paclitaxel-initiated, controlled polymerization of lactide for the formulation of polymeric nanoparticulate delivery vehicles." Angewandte Chemie International Edition 47.26 (2008): 4830-4834. (Year: 2008).*
Smith, Anton AA, et al. "Nanoparticles presenting potent TLR7/8 agonists enhance anti-PD-L1 immunotherapy in cancer treatment." Biomacromolecules 21.9 (Aug. 2020): 3704-3712. (Year: 2020).*
Roth et al. (2021) "Prolonged Codelivery of Hemagglutinin and a TLR7/8 Agonist in a Supramolecular Polymer-Nanoparticle Hydrogel Enhances Potency and Breadth of Influenza Vaccination" entire document especially p. 1889, Para 1; p. 1892, Para 4; p. 1893, Para 2; p. 1895, Para 1; Figure 4b.
Kakwere et al. (2021) "Systemic Immunotherapy with Miceller Resiquimod—Polymer Conjugates Triggers a Robust Antitumor Response in a Breast Cancer Model" Advance Healthcare Materials, vol. 10, Issue10; 2100008 pp. 1-5.

* cited by examiner

*Primary Examiner* — Bethany P Barham
*Assistant Examiner* — Peter Anthopolos
(74) *Attorney, Agent, or Firm* — Bozicevic, Field & Francis LLP; Andrew R. Guzman

(57) ABSTRACT

Compositions and methods are provided relating to TLR agonist nanoparticle vaccine adjuvant formulations.

17 Claims, 19 Drawing Sheets

TOLL-LIKE RECEPTOR AGONIST-NANOPARTICLE VACCINE ADJUVANT

CROSS REFERENCE TO RELATED APPLICATION

The present application claims the benefit of and priority to U.S. Provisional Patent Application No. 63/177,709 filed Apr. 21, 2021, the entire disclosure of which is hereby incorporated by reference in its entirety

BACKGROUND

Vaccines are our ultimate weapons against infectious diseases and have saved countless lives since their first use in the late $18^{th}$ century. An adjuvant is a key to enhance vaccine-induced immunity. It can improve, prolong, and modulate immune responses to vaccine antigens to maximize protective immunity. The current clinically used vaccine adjuvant was primarily focused on the use of alum including aluminum hydroxide and aluminum phosphate. However, the alum-adjuvant vaccine, especially for those using inactivated, subunit, or purified recombinant proteins, often required multiple doses for protection to be achieved and failed to induce the broad antibody responses, which are of great importance for developing HIV vaccine and a universal influenza vaccine. Thus, the use of novel adjuvants and delivery systems to replace alum has become critical.

Among a variety of toll-like receptors (TLRs)-targeting adjuvant candidates, TLR7 and/or TLR8 have attracted tremendous interest. Though potent, these agonists are not easily translated into clinical use due to their low tolerability profile when tested in humans. Common systemic side effects are often observed, including injection site reactogenicity and flu-like symptoms (fever, headache, and malaise) that correlate with systemic immune activation, such as high concentrations of numerous cytokines in the blood.

There is a great interest in improving vaccine adjuvants and reducing undesirable side-effects.

SUMMARY OF THE INVENTION

TLR agonist-nanoparticle vaccine adjuvants are provided herein, which adjuvants find use in the formulation of vaccines, e.g. vaccines specific for pathogens including, without limitation, viral, bacterial and protozoan pathogens. In some embodiments a vaccine is specific for a viral pathogen. In some embodiments the viral pathogen is an influenza virus. In some embodiments the viral pathogen is a SARS-CoV2 virus.

The nanoparticle adjuvant of the disclosure comprises a TLR agonist conjugated to a polymer through cleavable linkages. In some embodiments the cleavable linkage is ester linker. Other linkers include, for example, pH-sensitive amino ester linkers, redox-responsive disulfide linkers, etc. In some embodiments the polymer is polylactide (PLA). The polymer is formed into nanoparticles, where the TLR agonist is released in a sustained manner, reducing undesirable toxicity. Once internalized into cells, the release rate of the agonist from the nanoparticles is accelerated by the low pH in endosomes, leading to robust activation of the intracellular TLR7/8 receptors. In some embodiments the TLR agonist activates an endosomal TLR. In some embodiments the TLR agonist is a TLR7 agonist. In some embodiments the TLR agonist is a TLR8 agonist. In some embodiments the TLR agonist is gardiquimod.

In some embodiments the TLR agonist is conjugated to a polylactide (PLA) polymer through an ester linkage, where the conjugate has a structure:

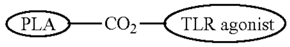

The number of lactide subunits in the polymer may range from about 5, about 10, about 15, up to about 100, up to about 50, up to about 30, up to about 25. In some embodiments, e.g. where the TLR agonist is gardiquimod, the conjugate has a structure:

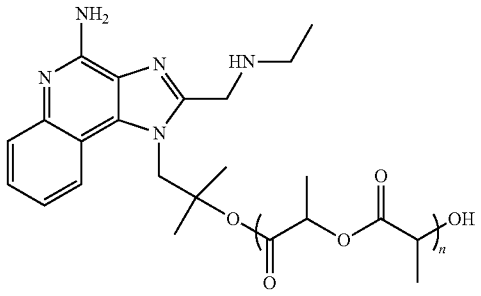

where n is from about 5 to 100.

The TLR agonist-polymer conjugate can self-assemble, or co-nanoprecipitate with a second polymer, to form biodegradable nanoparticles. In some embodiments the second polymer comprises polyethylene glycol (PEG) or a conjugate thereof. In some embodiments the second polymer comprises PEG conjugated to poly-lactic acid, poly-glycolic acid, or poly(lactic-co-glycolic acid). In some embodiments the second polymer is PEG-PLGA.

In some embodiments the vaccine composition comprises a biodegradable nanoparticle from about 10 nm in diameter to about 100 nm in diameter, and may be from about 25 nm to about 100 nm in diameter, from about 50 to about 100 nm, from about 75 nm in diameter to about 100 nm in diameter, from about 60 nm to about 85 nm in diameter. A narrow size distribution can be achieved, where the standard deviation of diameter is less than about 25 nm, less than about 15 nm, less than about 10 nm. The size of nanoparticles can be tuned by changing the organic solvents in which the TLR agonist conjugated polymer is dissolved to generate larger particles, e.g. from about 100 nm up to about 1 μm; up to about 750 nm, up to about 500 nm, up to about 250 nm.

An antigen (immunogen) of interest may be co-precipitated with the polymers to form the nanoparticle. The antigen may be conjugated to the nanoparticles. The antigen may be co-formulated with the nanoparticles in the absence of a physical linkage. Alternatively, the antigen can be adsorbed on alum and co-administrated with the nanoparticles.

In some embodiments, methods are provided for stimulating an immune response to a pathogen antigen of interest, the method comprising administering to an individual mammal an effective dose or series of doses of a vaccine composition comprising a TLR agonist-nanoparticle vaccine adjuvant and an antigen of interest. The particles may be provided in a pharmaceutically acceptable excipient.

Relative to the free TLR agonist, the adjuvants disclosed herein have improved in vivo retention, draining lymph node (LN) accumulation, and cellular uptake of the TLR agonist by antigen presenting cells, leading to persistent mobilization and activation of dendritic cells and cells of monocytic lineage in draining LNs. The constant activation of innate immune cells leads to subsequent early and robust induction of T follicular helper cell response, which boosts early geminal center response to control antigen-specific antibody production. Efficient humoral and T cell responses are elicited.

In some embodiments, a virus antigen vaccine adjuvanted with an effective dose of a TLR agonist-nanoparticle adjuvants of the disclosure is provided. In some embodiments, a method of enhancing a recipient response to a vaccine is provided, where the vaccine comprises an effective dose of a TLR agonist-nanoparticle adjuvant of the disclosure. Advantages of the disclosed adjuvant include, for example, elicitation of B cell differentiation and antibody response to the vaccine with higher antigen-specific antibody-secreting cells (ASCs) in the bone marrow, combined with minimal systemic immune toxicity relative to, for example, alum adjuvant. Toxicity may be monitored, for example, by measuring the expression of cytokines produced in response to immunization with a vaccine relative to a reference adjuvant where the adjuvant of the disclosure results in relatively lower levels of one or more cytokines such as, e.g. IFNα, CXCL1 (groA), MIP1A, Rantes, IL-17A, IL-31, IL-6, IP-10, MCP1, MIP1B, etc.

In a method of enhancing a response to an antigen, e.g. a virus antigen, the method may comprise administering one or a series, e.g. 2, 3, or more administrations, of a vaccine in combination with an effective dose of an adjuvant on the disclosure. Administration may be intramuscular, sub-cutaneous, intranasal or other pulmonary delivery, and the like. The administration can provide for efficient humoral and T cell responses with minimal systemic toxicity.

The effective dose of the adjuvant can be calculated, for example, by the dose of the TLR agonist that is provided in the nanoparticles, where an effective dose may be, from about a unit dose of 0.1 μg for an adult human recipient, from about 0.5 μg, from about 1 μg, from about 2 μg, from about 3 μg, from about 5 μg, from about 10 μg, from about 25 μg, up to about 1 mg, up to about 800 μg, up to about 600 μg, up to about 400 μg, up to about 200 μg, up to about 100 μg, up to about 50 μg.

In some embodiments, methods are provided for generating polymers comprising a plurality of ester linked TLR agonist moieties. In such methods, the TLR agonist, for example gardiquimod, is used as the initiator to initiate ring-opening polymerization (ROP) reaction of lactide to form a poly-lactide polymer comprising a defined level of agonist loading. The agonist may be from about 5% to about 25% wt. % of the polymer, e.g. from about 7.5% to about 20%, from about 10% to about 17.5%, from about 12.5% to about 15%. This method provides for quantitative incorporation of the agonist into PLA polymers, with precisely controlled composition and molecular weights.

Other aspects and features will be readily apparent to the ordinarily skilled artisan upon reading the present disclosure.

BRIEF DESCRIPTION OF THE DRAWINGS

The invention is best understood from the following detailed description of exemplary embodiments when read in conjunction with the accompanying drawings. It is emphasized that, according to common practice, the various features of the drawings are not necessarily to-scale. On the contrary, the dimensions of the various features are arbitrarily expanded or reduced for clarity. Included in the drawings are the following figures.

DETAILED DESCRIPTION OF THE EMBODIMENTS

Figure 1A:
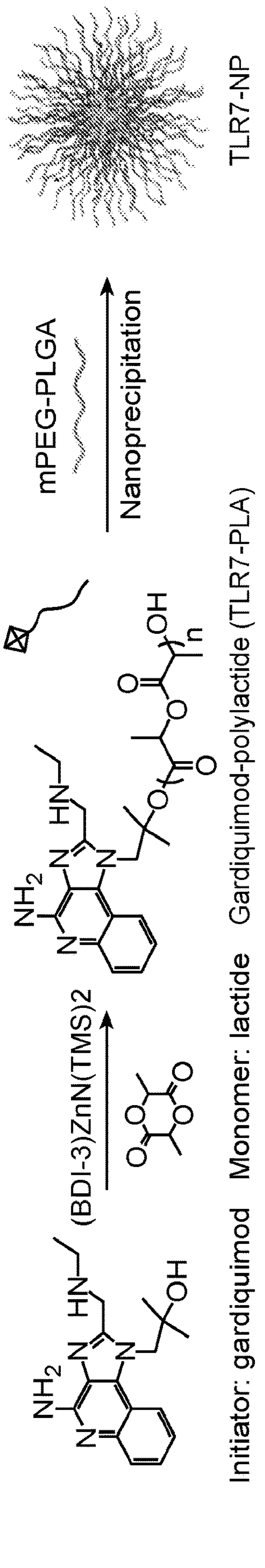
FIGS. 1A-1D. Synthesis, formulation and characterization of gardiquimod-polylactide nanoparticles (TLR7-NP). (a) Schematic illustration of synthesizing TLR7-PLA polymer conjugate via gardiquimod initiated ring-opening polymerization of lactide and preparing TLR7-NPs through nanoprecipitation. (b) Hydrodynamic sizes of TLR7-NPs characterized by DLS analysis. (c) The UV absorbance of TLR7-PLA polymer, TLR7 agonist (gardiquimod), and TLR7-NPs after release measured by UV spectrometer at λ=321 nm. (d) Release kinetic profile of TLR7 agonist (gardiquimod) from TLR7-NPs in PBS buffer at pH 5.0 and pH 7.4.

It is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the polypeptide" includes reference to one or more polypeptides and equivalents thereof known to those skilled in the art, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

A used herein, the term "immune response" and grammatical equivalents refer to a response by the immune system of a subject. For example, immune responses include, but are not limited to, a detectable alteration, e.g., increase, in Toll-like receptor (TLR) activation; lymphokine, e.g., Th1 or Th2 type cytokines, or chemokine, expression and/or secretion; macrophage activation; dendritic cell activation; T cell activation, e.g., CD4+ or CD8+ T cells; NK cell activation; and/or B cell activation, e.g., antibody generation and/or secretion. Additional examples of immune responses include binding of an immunogen to an MHC molecule and inducing a cytotoxic T lymphocyte response; inducing a B cell response, e.g., antibody production; and/or T-helper lymphocyte response; and/or a delayed type hypersensitivity (DTH) response against the antigen from which the immunogenic polypeptide is derived; expansion of cells of the immune system; and increased processing and presentation of antigen by antigen presenting cells.

An immune response may be to immunogens that the subject's immune system recognizes as foreign, e.g., non-self antigens from microorganisms, e.g., pathogens, or self-antigens recognized as foreign. Thus, it is to be understood that, as used herein, "immune response" refers to any type of immune response, including, but not limited to, innate immune responses, cell-mediated immune responses, and humoral immune responses. The term "immune response" is meant to encompass all aspects of the capability of a subject's immune system to respond to antigens and/or immunogens including the initial response to an immunogen as well as acquired, e.g., memory, responses that are a result of an adaptive immune response.

Some embodiments of the invention provide a method of stimulating an immune response in a mammal, which can be a human or a preclinical model for human disease, e.g. mouse, ape, monkey etc. "Stimulating an immune response" includes, but is not limited to, inducing a therapeutic or prophylactic effect that is mediated by the immune system of the mammal. More specifically, stimulating an immune response in the context of the invention refers to eliciting cellular or humoral immune responses, thereby inducing downstream effects such as production of antibodies, antibody heavy chain class switching, maturation of APCs, and stimulation of cytolytic T cells, T helper cells and both T and B memory cells.

The terms "humoral immunity" and "humoral immune response" refer to the form of immunity in which antibody molecules are produced in response to antigenic stimulation.

The terms "cell-mediated immunity" and "cell-mediated immune response" are meant to refer to the immunological defense provided by lymphocytes, such as that defense provided by T cell lymphocytes when they come into close proximity to their victim cells. A cell-mediated immune response normally includes lymphocyte proliferation. When "lymphocyte proliferation" is measured, the ability of lymphocytes to proliferate in response to a specific antigen is measured. Lymphocyte proliferation is meant to refer to B cell, T-helper cell or cytotoxic T-lymphocyte (CTL) cell proliferation.

As used herein, the term "a composition for inducing an immune response" refers to a composition, e.g. a vaccine composition, that, once administered to a subject, e.g., once, twice, three times or more, separated by a period of time, e.g. weeks, months or years, stimulates, generates and/or elicits an immune response in the subject resulting in total or partial immunity to a microorganism (e.g., pathogen) capable of causing disease. In some embodiments of the invention, the composition comprises one or more antigens/immunogens together with an adjuvant formulation disclosed herein, formulated for administration, e.g., via injectable route such as intradermal, intramuscular, subcutaneously, etc., mucosal route, e.g., nasally or vaginally, or other route to a subject. In further embodiments, the immunogenic composition comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate immune response or an acquired immune response that decreases the infectivity, morbidity, or onset of mortality in a subject caused by exposure to a pathogenic microorganism, or that prevents infectivity, morbidity, or onset of mortality in a subject caused by exposure to a pathogenic microorganism.

The term "eliciting an immune response" is used herein generally to encompass induction and/or potentiation of an immune response. The term "inducing an immune response" refers to an immune response that is stimulated, initiated, or induced. The term "potentiating an immune response" refers to a pre-existing immune response that is improved, furthered, supplemented, amplified, enhanced, increased or prolonged.

The expression "enhanced immune response" or similar means that the immune response is elevated, improved or enhanced to the benefit of the host relative to the prior immune response status, for example, before the administration of an immunogenic composition of the invention, or in the absence of an adjuvant of the disclosure.

The term "immunogenic amount" refers to an amount of antigenic compound sufficient to stimulate an immune response, when administered with a subject immunogenic composition, as compared with the immune response elicited by the antigen in the absence of the polynucleotide adjuvant.

The term "effective dose" or "effective dosage" is defined as an amount sufficient to achieve or at least partially achieve the desired effect. The term "therapeutically effective dose" is defined as an amount sufficient to induce an immune response to the antigen and may at least at least partially arrest an infectious disease and its complications in a patient already suffering from the disease. Amounts effective for this use will depend upon the severity of the disorder being treated and the general state of the patient's own immune system.

The term "an amount effective to induce an immune response" of a composition for inducing an immune response comprising a nanoparticle adjuvant formulated for administration, refers to the dosage level required when administered to a subject to stimulate, generate and/or elicit an immune response in the subject. An effective amount can be administered in one or more administrations via the same or different route, applications or dosages and is not intended to be limited to a particular formulation or administration route. Accordingly, a "therapeutically effective amount" or "effective dose" of a composition for inducing an immune response refers to the dosage level or amount of a composition required when administered to a subject to stimulate, generate and/or elicit a therapeutic benefit in a subject. A therapeutically effective amount can be administered in one or more administrations, via the same or different route, applications or dosages and is not intended to be limited to a particular formulation or administration route.

By the term "vaccine" as used herein, is meant a composition comprising (i) an effective dose of an antigen; and (ii) a TLR agonist nanoparticle adjuvant, which, when administered to a subject, induces cellular or humoral immune responses as described herein. Vaccines may comprise, for example, antigenic polypeptides, nucleic acids encoding such antigenic polypeptides, or other antigenic substances, e.g. carbohydrates, etc.

Vaccine compositions may include an aqueous medium, pharmaceutically acceptable inert excipient such as lactose, starch, calcium carbonate, and sodium citrate. Vaccine compositions may also include an adjuvant, for example Freud's adjuvant. Vaccines may be administered alone or in combination with a physiologically acceptable vehicle that is suitable for administration to humans. Vaccines may be delivered orally, parenterally, intramuscularly, intranasally or intravenously. Oral delivery may encompass, for example, adding the compositions to the feed or drink of the mammals. Factors bearing on the vaccine dosage include, for example, the weight and age of the mammal. Compositions for parenteral or intravenous delivery may also include emulsifying or suspending agents or diluents to control the delivery and dose amount of the vaccine.

As appreciated by skilled artisans, vaccine compositions are suitably formulated to be compatible with the intended route of administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH of the composition can be adjusted with acids or bases, such as hydrochloric acid or sodium hydroxide. Systemic administration of the composition is also suitably accomplished by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories.

"Polypeptide" and "protein" as used interchangeably herein, can encompass peptides and oligopeptides. Where "polypeptide" is recited herein to refer to an amino acid sequence of a naturally-occurring protein molecule, "polypeptide" and like terms are not necessarily limited to the amino acid sequence to the complete, native amino acid sequence associated with the recited protein molecule, but instead can encompass biologically active variants or fragments, including polypeptides having substantial sequence similarity or sequence identify relative to the amino acid sequences provided herein. In general, fragments or variants retain a biological activity of the parent polypeptide from which their sequence is derived. Polypeptides may be, for example, at least 8 amino acids in length, at least 10, at least 12, at least 14, at least 16, at least 18, at least 20, at least 22, at least 24, and may be at least 30, at least 40, at least 50, at least 75, at least 100 or more amino acids in length.

Polypeptides suitable for use can be obtained from any species, e.g., mammalian or non-mammalian (e.g., reptiles, amphibians, avian (e.g., chicken)), particularly mammalian, including human, rodent (e.g., murine or rat), bovine, ovine, porcine, murine, or equine, particularly rat or human, from any source whether natural, synthetic, semi-synthetic or recombinant. In general, polypeptides comprising a sequence of a human polypeptide are of particular interest.

The term "derived from" indicates molecule that is obtained directly from the indicated source (e.g., when a protein directly purified from a cell, the protein is "derived from" the cell) or information is obtained from the source, e.g. nucleotide or amino acid sequence, from which the molecule can be synthesized from materials other than the source of information.

The term "isolated" indicates that the recited material (e.g, polypeptide, nucleic acid, etc.) is substantially separated from, or enriched relative to, other materials with which it occurs in nature (e.g., in a cell). A material (e.g., polypeptide, nucleic acid, etc.) that is isolated constitutes at least about 0.1%, at least about 0.5%, at least about 1% or at least about 5% by weight of the total material of the same type (e.g., total protein, total nucleic acid) in a given sample.

The terms "subject" and "patient" are used interchangeably herein to mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest. As will be evidence from the context in which the term is used, subject and patient refer to a subject or patient susceptible to infection.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds calculated in an amount sufficient to produce the desired effect in association with a pharmaceutically acceptable diluent, carrier or vehicle. The specifications for the novel unit dosage forms depend on the particular compound employed and the effect to be achieved, and the pharmacodynamics associated with each compound in the host.

A "pharmaceutically acceptable excipient", "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and is usually free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by cell culture, uncontaminated by other immunoglobulins. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made in an immortalized B cell or hybridoma thereof, may be made by recombinant DNA methods, including without limitation yeast display.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix, e.g. a particle, to which the vaccine components can adhere, be conjugated to, or be encapsulated within.

An "effective amount of an antigenic compound" refers to an amount of antigenic compound which, in optional combination with an adjuvant, will cause the subject to produce a specific immunological response to the antigenic compound.

Adjuvants and TLR Agonists

The term "adjuvant" or "vaccine adjuvant" as used herein refers to a substance or combination of substances that non-specifically enhances the immune response to an antigen, in particular the TLR agonist nanoparticle adjuvants disclosed herein. Adjuvants are effective in stimulating protective immunity.

The innate immunity is composed of several families of pattern recognition receptors (PPRs). The latter receptors serve to identify pathogen-associated molecular patterns (PAMPs) and danger-associated molecular patterns (DAMPs). The PPRs act as the primary defense against pathogenic entities and control the activation and progression of the adaptive immunity by activating the production not only of pro-inflammatory cytokines, chemokines and interferons, but also B and T cells. Among the PPRs, the Toll-like Receptors (TLRs) are of interest.

TLRs are divided into two groups depending on their subcellular localization, which largely correlate with the type of molecular patterns they are able to recognize. Among endosomal TLRs, TLR7 and TLR8 have a high degree of sequence homology and function similarity. Both receptors recognize viral single-stranded RNAs, as well as synthetic tricyclic derivatives belonging to the imidazo[4,5-c]quinoline series, including without limitation resiquimod, a TLR7/8 agonist.

TLR7, TLR8 and TLR9 induce antiviral responses by the production of IFNα as well as pro-inflammatory cytokines. These three receptors use the MyD88 adapter protein to initiate the signaling pathways. The IRF7 transcription factor (Interferon regulatory factor 7) is responsible for the expression and production of IFNα. MyD88 interacts directly with IRF7 at the endosome. IRF7 also interacts with TRAF6, another adapter molecule that operates downstream of MyD88, and after receptor activation (TLRs 7, 8 or 9), IRF7 is activated in a MyD88 and TRAF6 dependent manner.

TLR7 and TLR8 together mediate recognition of purine-rich ssRNA to elicit an immune response to pathogens recognized in the endosome. TLRs 7 and 8 are implicated in the recognition of naturally derived uridine-rich ssRNAs of influenza and HIV. In addition TLR7 and TLR8 recognize bacterial RNA. Furthermore, TLR7 and 8 are expressed in human plasmacytoid DCs (pDCs), in T and B cells, monocytes and macrophages. Naïve human B cells express low levels of TLR7 and, whereas activated and memory human B cells also express a broader range of TLRs including TLR7. B cell intrinsic TLR7 signaling may play a role in B cell responses during chronic infections which could be used to activate memory B cells and boost humoral immune responses during immunization. Synthetic small molecules agonists that activate TLRs 7 and 8 are useful as adjuvants in the formulations described herein.

For a review of TLR7/8 agonists, see, for example, Patinote et al. (2020) Eur J Med Chem. 193:112238, herein specifically incorporated by reference. Examples of agonists include, without limitation, Bropirimine (2-amino-5-bromo-6-phenylpyrimidin-4-ol); N-4-butyl-6-methyl-5-(3-morpholinopropyl)-pyrimidine-2,4-diamine with simultaneous TLR7 and TLR8 agonist activities; 1-pentyl-4-phenyl-1H-imidazol-2-amine; SM-360320 is a TLR7 agonist; SM-276001 is a selective and potent TLR7 agonist; TMX-202 is a second-generation SM-360320 prodrug, which conjugates the TLR7 ligand to a C12 phospholipid via a benzoic acid functional group. TMX-302 and TMX-306 are PEGylated SM-360320 purine-like compounds characterized by TLR7 partial agonist activity; SZU-101; CL264 is a TLR7 specific agonist; CL307 links a spermine to CL264; AdiFectin™ (CL347); Adilipoline™ (CL413) is a derivative obtained by linearly linking a hydroxyadenine derivative with the terminal acid function of Pam2CSK4; CL531 corresponds to the conjugation of a hydroxyadenine derivative to the lateral chain of the second lysine of Pam2CSK4; CL572 contains a monoacyl-ethyl-cystein group grafted to a hydroxyadenine via a glutamic acid derivative; DSR-6434 is a specific TLR7 agonist; DSR-29133 is a TLR7-selective agonist; loxoribine and isatoribine activate immune cells exclusively via TLR7; Selgantolimod; SC1 (Pluripotin) is a TLR7 agonist; VTX-2337 (also known as Motolimod) is a selective and potent agonist of TLR 8; VTX-294 is a potent TLR8 agonist; VTX-763 is a TLR8 agonist; VTX-463 is a dual TLRs 7/8 agonist; TL8-506 is a TLR8 ligand; Imiquimod is a tricyclic nitrogen molecule belonging to the imidazo[4,5-c]quinoline series activating TLR7; Resiquimod is an imidazo[4,5-c]quinoline compound that activates TLR7 and TLR8; CL097 is TLR7 and TLR8 agonist; Compound 3M-001; 3M-002; Compound 3M-003 and 3M-011 are an agonist of both TLR7 and TLR8; Telratolimod is a TLR7/8 agonist; Gardiquimod is an agonist of TLR7 but not of human TLR8; LHC165 is a TLR7 agonist; MCT465 is a high molecular weight synthetic double-stranded RNA (dsRNA) that activates TLRs 3/7/8 signaling; CV8102 is a ssRNA-based TLRs 7/8 agonist.

CL413, CL531, selgantolimod, resiquimod, gardiquimod, and 3M-003 can be directly used for initiation of ring-opening polymerization as disclosed herein. Other agonists as described above can be chemically modified with the introduction of hydroxyl group on the side chain to be compatible with this method.

The dose of agonist may be within current clinical practice, for example CL413 at 50 pg-10 μg/ml (~30 pM-10 μM) for a human unit dose; CL531 at 5 pg-10 μg/ml (~3 pM-10 μM) for a human unit dose; Selgantolimod up to 3 mg per dose; Resiquimod from 10 ng-10 μg/ml with clinical trials of up to 0.02 mg/kg; Gardiquimod from 0.1-3 μg/ml in a unit dose.

TLR agonists in clinical trials include, for example:

| Ligand | TLR | Clinical Trial Identification |
|---|---|---|
| 852A (PF-04878691, S-32865 3M852A) | 7 | NCT00319748 |
| Imiquimod, R837 | 7 | NCT00453050 |
| Resiquimod, R848 | 7/8 | NCT01737580 |
| AZD8848, DSP-3025, AZD-3025 | 7 | NCT01124396 |
| GSK2245035 | 7 | NCT01607372 |
| GS-9620 vesatolimod | 7 | NCT02166047 |
| RO7020531 | 7 | NCT03530917 |
| RO6864018 (ANA773, ANA773, RG7795) | 7 | NCT02015715 |
| RO6871765 or RO7011785 | 7 | NCT02498275 |
| DSP-0509 | 7 | NCT03416335 |
| NJH395 | 7 | NCT03696771 |
| BNT411 | 7 | NCT04101357 |
| TQ-A3334, JNJ-4964, AL-034 | 7 | NCT04180150 |
| LHC165 | 7 | NCT03301896 |
| Hydroxychloroquine | 7/9 | NCT01601028 |
| MEDI9197 | 7/8 | NCT02556463 |
| NKTR-262 | 7/8 | NCT03435640 |
| CV8102 | 7/8 | NCT03203005 |
| VTX-2337, Motolimod | 8 | NCT01334177 |
| VTX-2337 | 8 | NCT03906526 |
| GS-9688 | 8 | NCT03615066 |

Antigens

As used herein, the term "antigenic compound" refers to any substance that can be recognized by the immune system (e.g., bound by an antibody or processed so as to elicit a cellular immune response) under appropriate conditions.

An "antigen" as used herein includes but is not limited to cells; cell extracts; proteins; lipoproteins; glycoproteins; nucleoproteins; polypeptides; peptides; polysaccharides; polysaccharide conjugates; peptide mimics of polysaccharides; lipids; glycolipids; carbohydrates; viruses; viral extracts; bacteria; bacterial extracts; fungi; fungal extracts; multicellular organisms such as parasites; and allergens. In some embodiments of the invention the antigen is a polypeptide, e.g. a native polypeptide; a polypeptide produced by recombinant methods, including in vitro cell free synthesis, bacterial and prokaryotic expression systems; and the like.

Vaccines can benefit from the inclusion of adjuvants to boost responses in populations with poor immune responses; this includes patients who are immunosuppressed due to either primary immunodeficiencies, transplant treatment or infection. Adjuvants can improve immune responses in the very young and the very old. Further, some antigens are less immunogenic than others, particularly vaccines containing recombinant proteins, and benefit from adjuvants.

Adjuvants can also accelerate responses to the vaccine, for example during a pandemic. Most vaccines require more than one administration to reach protective levels in recipients; the addition of an adjuvant can elevate the response to the first dose and push it over the protective threshold. Adjuvants can also change the pattern of cytokines and chemokines released, leading to the recruitment of different cells.

Adjuvants can also be used for mucosal delivery of vaccines. Through the induction of local immunity at sites of infection, mucosal vaccination may be more appropriate than systemic vaccination. However, mucosal surfaces are much harder to vaccinate for a number of reasons—they are broadly tolerogenic and they also have mechanical (cilia, gap junctions), chemical (mucus) and biochemical (proteolytic enzymes) barriers to antigen. Specific adjuvants may be required to protect the antigen in this environment and to induce a local immune response.

In some embodiments, a vaccine composition comprises an antigen composition, e.g. a polypeptide, whole virus, etc., and an adjuvant of the disclosure. In some such embodiments the antigen is an inactivated pathogen vaccine. In some such embodiment the antigen is a protein subunit antigen, e.g. a recombinantly produced polypeptide, which usually exhibit an extremely favorable safety profile but can require multiple boost doses and elicit low grade cellular responses.

In some embodiments the antigen in a pathogen antigen, where the term "pathogen" refers to any infectious microbes causing disease in an organism. In one embodiment, the pathogens comprise bacteria, fungi, archaea (e.g., methanogens, halophiles, thermophiles, and psychrophiles), protists (e.g., *Plasmodium, Entamoeba histolytica, Trypanosoma brucei, Giardia lamblia*), viruses, prions (e.g., PrPres and PrPSc), microscopic plants (e.g., *Shewanella algae, Shewanella putrefaciens*, and *Shewanella xiamenensis*), and/or microscopic animals (e.g., plankton and planarian). In some embodiments, viruses include but are not limited to RNA viruses such as flaviviruses, picornaviruses, rhabdoviruses, filoviruses, retroviruses (including lentiviruses such as HIV-1 and HIV-2), coronaviruses, e.g. SARS-CoV1, SARS-CoV2, SARS-MER, etc.; influenza viruses; etc. or DNA viruses such as adenoviruses, poxviruses, herpes viruses, cytomegaloviruses, hepadnaviruses, or others.

Some examples of bacteria for vaccines include, for example, Aceinetobacter *calcoaceticus, Acetobacter paseruianus, Actinobacillus pleuropneumoniae, Aeromonas hydrophila, Alicyclobacillus acidocaldarius, Arhaeglobus fulgidus, Bacillus pumilus, Bacillus stearothermophillus, Bacillus subtilis, Bacillus thermocatenulatus, Bordetella bronchiseptica, Burkholderia cepacia, Burkholderia glumae, Campylobacter coli, Campylobacter fetus, Campylobacter jejuni, Campylobacter hyointestinalis, Chlamydia psittaci, Chlamydia trachomatis, Chlamydophila* spp., Chromobacterium *viscosum, Erysipelothrix rhusiopathieae, Listeria monocytogenes, Ehrlichia canis, Escherichia coli, Haemophilus influenzae, Haemophilus somnus, Helicobacter suis, Lawsonia intracellularis, Legionella* pneumophilia, Moraxellsa sp., Mycobactrium *bovis, Mycoplasma hyopneumoniae, Mycoplasma mycoides* subsp. *mycoides* LC, *Clostridium perfringens, Odoribacter denticanis, Pasteurella* (Mannheimia) *haemolytica, Pasteurella multocida, Photorhabdus luminescens, Porphyromonas gulae, Porphyromonas gingivalis, Porphyromonas salivosa, Propionibacterium acnes, Proteus vulgaris, Pseudomnas wisconsinensis, Pseudomonas aeruginosa, Pseudomonas fluorescens* C9, *Pseudomonas fluorescens* SIKW1, *Pseudomonas fragi, Pseudomonas luteola, Pseudomonas oleovorans, Pseudomonas* sp B11-1, Alcaliges *eutrophus, Psychrobacter immobilis, Rickettsia prowazekii, Rickettsia rickettsia, Salmonella typhimurium, Salmonella bongori, Salmonella enterica, Salmonella dublin, Salmonella typhimurium, Salmonella choleraseuis, Salmonella newport, Serratia marcescens, Spirlina platensis, Staphlyococcus aureus, Staphyloccoccus epidermidis, Staphylococcus hyicus, Streptomyces albus, Streptomyces cinnamoneus, Streptococcus suis, Streptomyces exfoliates, Streptomyces scabies, Sulfolobus acidocaldarius*, Syechocystis sp., *Vibrio cholerae, Borrelia burgdorferi, Treponema denticola, Treponema minutum, Treponema phagedenis, Treponema refringens, Treponema vincentii, Treponema* palladium, and Leptospira species, such as the known pathogens *Leptospira canicola, Leptospira grippotyposa, Leptospira hardjo, Leptospira borgpetersenii hardjo-bovis, Leptospira borgpetersenii hardjo-prajitno, Leptospira interrogans, Leptospira icterohaemorrhagiae, Leptospira pomona*, and *Leptospira bratislava*, and combinations thereof.

Examples of viruses suitable for vaccines, for example, SARS-Cov1, SARS-Cov2, and other coronaviruses, Avian herpesviruses, Bovine herpesviruses, Canine herpesviruses, Equine herpesviruses, Feline viral rhinotracheitis virus, Marek's disease virus, Ovine herpesviruses, Porcine herpesviruses, Pseudorabies virus, Avian paramyxoviruses, Bovine respiratory syncytial virus, Canine distemper virus, Canine parainfluenza virus, canine adenovirus, canine parvovirus, Bovine Parainfluenza virus 3, Ovine parainfluenza 3, Rinderpest virus, Border disease virus, Bovine viral diarrhea virus (BVDV), BVDV Type I, BVDV Type II, Classical swine fever virus, Avian Leukosis virus, Bovine immunodeficiency virus, Bovine leukemia virus, Bovine tuberculosis, Equine infectious anemia virus, Feline immunodeficiency virus, Feline leukemia virus (FeLV), Newcastle Disease virus, Ovine progressive pneumonia virus, Ovine pulmonary adenocarcinoma virus, Canine coronavirus (CCV), pantropic CCV, Canine respiratory coronavirus, Bovine coronavirus, Feline Calicivirus, Feline enteric coronavirus, Feline infectious peritonitis, virus, Porcine epidemic diarrhea virus, Porcine hemagglutinating encephalomyletitis virus, Porcine parvovirus, Porcine Circovirus (PCV) Type I, PCV Type II, Porcine Reproductive and Respiratory Syndrome (PRRS) Virus, Transmissible gastroenteritis virus, Turkey coronavirus, Bovine ephemeral fever virus, Rabies, Rotovirus, Vesicular stomatitis virus, lentivirus, Avian influenza, Rhinoviruses, Equine influenza virus, Swine influenza virus, Canine influenza virus, Feline influenza virus, Human influenza virus, Eastern Equine encephalitis virus (EEE), Venezuelan equine encephalitis virus, West Nile virus, Western equine encephalitis virus, human immunodeficiency virus, human papilloma virus, varicella zoster virus, hepatitis B virus, rhinovirus, and measles virus, and combinations thereof.

Examples of parasites suitable for vaccines include, for example, *Anaplasma, Fasciola hepatica* (liver fluke), Coccidia, *Eimeria* spp., *Neospora caninum, Toxoplasma gondii, Giardia, Dirofilaria* (heartworms), *Ancylostoma* (hookworms), *Trypanosoma* spp., *Leishmania* spp., *Trichomonas* spp., *Cryptosporidium parvum, Babesia, Schistosoma, Taenia, Strongyloides, Ascaris, Trichinella, Sarcocystis*, Hammondia, and Isopsora, and combinations thereof. Also contemplated are external parasites including, but not limited to, ticks, including *Ixodes, Rhipicephalus, Dermacentor, Amblyomma, Boophilus, Hyalomma*, and *Haemaphysalis* species, and combinations thereof.

Antigens may be exogenous (e.g., from a source other than the individual to whom the antigen is administered, e.g., from a different species) or endogenous (e.g., originating from within the host, e.g., a diseased element of body, a virus infected cell producing antigen, and the like). Antigens may be native (e.g., naturally-occurring); synthetic; or recombinant. Antigens include crude extracts; whole cells; and purified antigens, where "purified" indicates that the antigen is in a form that is enriched relative to the environment in which the antigen normally occurs and/or relative to the crude extract, for example, a cultured form of the antigen. The present invention is directed to a composition further comprising an antigen or an antigenic peptide (e.g., epitope). Preferably, the antigen or antigenic peptide is recognized by autologous T cells. Any antigen may be used in the present invention that is displayed or detected on the surface of infected cells. The antigen may be a wild type antigen or mutated relative to its wild type; or may be differentially post-translationally modified relative to the wild type.

Antigens recognized by T cells, whether helper T lymphocytes or CTL, are not recognized as intact proteins, but rather as small peptides that associate with class I or class II MHC proteins on the surface of cells. During the course of a naturally occurring immune response, antigens that are recognized in association with class I or II MHC molecules on antigen presenting cells (APCs) are acquired from outside the cell, internalized, and processed into small peptides that associate with the class I or II MHC molecules.

Antigens that give rise to proteins that are recognized in association with class I MHC molecules are generally proteins that are produced within the cells, and these antigens are processed and associate with class I MHC molecules. It is now understood that the peptides that associate with given class I or class II MHC molecules are characterized as having a common binding motif, and the binding motifs for a large number of different class I and II MHC molecules have been determined. Synthetic peptides can also be synthesized that correspond to the amino acid sequence of a given antigen and that contain a binding motif for a given class I or II MHC molecule. These peptides can then be added to appropriate APCs, and the APCs can be used to stimulate a T helper cell or CTL response either in vitro or in vivo. The binding motifs, methods for synthesizing the peptides, and methods for stimulating a T helper cell or CTL response are all known and readily available to one of ordinary skill in the art.

Compositions comprising an antigen protein or peptide are, or can be, made synthetically or by purification from a biological source. They can be made recombinantly. Desirably they are in some embodiments at least 90% pure, in some embodiments at least 92% pure, in some embodiments at least 93% pure, in some embodiments at least 94% pure, in some embodiments at least 95% pure, in some embodiments at least 96% pure, in some embodiments at least 97% pure, in some embodiments at least 98% pure, and in some embodiments at least 99% pure. For administration to a human, they generally do not contain other components that might be harmful to a human recipient.

Under certain circumstances it can be desirable to add additional antigenic proteins or antigenic peptides to the composition, for example, to make a cocktail having the ability to stimulate an immune response in a number of different HLA type hosts. Alternatively, additional proteins and/or peptides can provide an interacting function within a single host, such as but not limited to an adjuvant function or a stabilizing function.

Influenza virus and vaccines. In some embodiments, the adjuvants disclosed herein are utilized in the formulation of influenza vaccines. Influenza viruses are members of the family Orthomyxoviridae, which are enveloped viruses with a genome of segmented negative-sense single-strand RNA segments. There are four genera of this family: types A, B, C and Thogotovirus, of which, however, only genera A and B are clinically relevant for humans. The genome segments of influenza A and B viruses are loosely encapsidated by the nucleoprotein, which capsids are encircled by the M1 matrix protein and by a host-derived lipid bilayer envelope in which the virus surface glycoproteins haemagglutinin (HA) and neuraminidase (NA) as well as the M2 matrix protein are embedded.

Influenza viruses rapidly evolve, leading to great variability, particularly for influenza A. According to the antigenic properties of their envelope proteins, influenza A viruses are subdivided into a number of subtypes: 16 different HA and 9 different NA subtypes have been identified so far. The nomenclature system follows the pattern H(x)N(y) including the host of origin, geographical location, strain number, and year of isolation. Influenza B viruses are not further divided into subtypes. The accumulation of point mutations leads to a step-by-step modification of the virus proteins, particularly HA and NA. The process of "antigen shift" (re-assortment) is defined as the exchange of whole genome segments, particularly HA genes, which can result from simultaneous infection of a cell by two different influenza A viruses.

Human influenza virus infections have a world-wide distribution. Seasonal influenza epidemics occur regularly both in the Northern and the Southern hemispheres each winter. Due to the seasonal shift, the winter influenza outbreak of the Southern hemisphere occurs during the summer of the Northern hemisphere. These influenza epidemics are estimated to cause approximately 500,000 deaths per year world-wide. Influenza pandemics are characterized by an influenza A subtype against which the majority of the human population is not immune, thus causing a world-wide epidemic, including the Spanish Flu of 1918 (H1N1), Asian influenza of 1957 (H2N2), and Hong Kong Flu of 1968 (H2N3).

Seasonal influenza (flu) vaccines are designed to protect against the four main groups of flu Type A and B viruses that research indicates are most likely to spread and cause illness among people during the upcoming flu season. All U.S. flu vaccines protect against a flu A(H1) virus, a flu A(H3) virus, a flu B/Yamagata lineage virus and a flu B/Victoria lineage virus. Each of these four vaccine virus components are selected based on data relating to which infection and spread of virus is present ahead of the flu season, performance of the previous year's vaccine, and cross-protection from the vaccine.

A large number of countries participate in year-round surveillance for flu viruses as part of the World Health Organization (WHO) Global Influenza Surveillance and Response System (GISRS). The WHO vaccine composition committee reviews global flu data and recommends specific vaccine viruses for trivalent (three-virus component) and quadrivalent (four-virus component) vaccines.

Candidate vaccine viruses (CVVs) must be tested and available in time to allow for manufacturers to produce the large amount of vaccine virus needed to make flu vaccine. CVVs are chosen to protect against the viruses likely to circulate during the upcoming season. Currently there are 26 licensed inactivated vaccines for influenza, of which 13 are routinely manufactured for each influenza season. The majority of the licensed vaccines are egg derived, and there are three manufacturing processes to recover and inactivate the virus: whole virus, split (where the virus has been disrupted by a detergent) and subunit (where the haemagglutinin and neuraminidase proteins have been further purified, removing other viral proteins). One manufacturer uses recombinant protein technology, expressing only the haemagglutinin protein from an insect cell line. In addition to the inactivated vaccines there are also three live attenuated vaccines with slightly different backbones: Fluenz/Flumist (AstraZeneca), Ultravac (Microgen) and Nasovac (Serum institute of India).

In healthy adults, inactivated influenza vaccines are mostly immunogenic. However, the ability of a vaccine to induce HAI titres against a specific virus does not necessarily lead to protection against the circulating strain in the subsequent flu season. Influenza vaccines have highly variable rates of efficacy; the biggest factor being the match or mismatch between the vaccine strains and the circulating strains.

Coronaviruses (CoVs) are single-stranded RNA viruses characterized by club-like spikes that can potentially cause severe respiratory disease in human, for which vaccines can utilize the adjuvants of the present disclosure. Severe acute respiratory syndrome (SARS) is caused by SARS-CoV. Middle East respiratory syndrome (MERS)-CoV continues to cause deaths. SARS-CoV-2 has spread globally. Coronavirus genomes encode non-structural and structural proteins, including spike (S), envelope (E), membrane (M), and nucleocapsid (N) proteins. The majority of the candidate vaccines for COVID-19 that employ administration of viral antigens or viral gene sequences aim to induce neutralizing antibodies against the viral spike protein (S), preventing uptake through the human ACE2 receptor and, therefore, blocking infection. Vaccine platforms include inactivated vaccines, recombinant protein vaccines, live-attenuated vaccines, viral vector (adenovirus) vaccines, DNA vaccines, and mRNA vaccines. Most SARS-CoV vaccines rely on spike protein sequences, although there is also interest in whole virus or N protein vaccines. There are a large number of SARS-CoV-2 sequence variants known in the literature, and available at, for example, Genbank. See for example, accession no. NC_045512, Wu et al. Nature. 2020 March; 579(7798):265-269 for the initial reference sequence.

SARS-CoV2 vaccines in development include nucleic acid vaccines, e.g. mRNA molecules that contains the information for the synthesis of a stabilized pre-fusion form of the SARS-CoV-2 Spike (S) protein, or the full-length SARS-CoV-2 spike protein, encapsulated in a lipid nanoparticle (LNP) vector that enhances uptake by host immune cells. The administered mRNA uses the host cell transcription and translation machinery to produce the viral antigen that is afterward presented in T lymphocytes and is also directly recognized by B lymphocytes of the host, thereby initiating an adaptive immune response directed against the S protein of the virus. DNA vaccines are also candidates.

A number of viral vaccines have been produced, including replication-defective human adenovirus serotype 5 vector (Ad5) to deliver the coding sequence for SARS-CoV-2 full-length S protein into host cells; and a debilitated chimpanzee adenovirus (ChAdOx1) platform to comprising the coding sequence of the wild-type SARS-CoV-2 Spike protein. The Sputnik V vaccine uses replication-defective Ad26 was selected to deliver the genetic information for Spike protein during the first vaccination and recombinant replication-defective Ad5 for the second. A replicating-defective adenovirus 26 based vector expressing the stabilized prefusion S protein of SARS-CoV-2 has been widely used.

Other SARS-CoV2 vaccines include adjuvanted purified, inactivated virus, inactivated with β-propiolactone. Inactivated vaccines commonly need several boost doses to produce strong immune responses and do not traditionally activate cellular responses, typically requiring the addition of adjuvants.

Similar to inactivated pathogen vaccines, protein subunit candidates usually exhibit an extremely favorable safety profile but require multiple boost doses and elicit low grade cellular responses. Included in this category is a prefusion full-length recombinant SARS-CoV-2 S glycoprotein nanoparticle expressed in a baculovirus-Sf9 system and is administered with an adjuvant. Another vaccine similar in design to quadrivalent flu vaccine uses a baculovirus expression system to express high levels of the S protein of SARS-CoV-2 in lepidopteran insect cells with AS03 (Adjuvant System 3) squalene-based adjuvant.

Virus like particle vaccines aim to combine the efficacy of attenuated pathogen vaccines with the excellent safety profile usually found in subunit vaccines. The VLP displays multiple copies of the target antigen on its surface and has a size that favors recognition and subsequent uptake from antigen-presenting cells, therefore promoting its efficient phagocytosis, processing, and presentation by dendritic cells, and inducing strong adaptive responses. This vaccine uses virus-transfected plant *Nicotiana benthamiana* to express the prefusion trimeric subunit form of the SARS-CoV-2 S-protein and assemble it on the surface of VLPs which are harvested and used for immunization.

Nanoparticles are formed from materials that are biodegradable and non-toxic. The antigen may be dispersed or encapsulated within the nanoparticle, linked to the nanoparticle, or formulated with the nanoparticle in the absence of physical linkage. Nanoparticles of the disclosure comprise a conjugate of a polymer, e.g. PLA, conjugated through an ester linkage to a TLR agonist. The nanoparticles may further comprise an additional polymer, where the nanoparticle is formed through co-precipitation of the polymers.

Some preferred biodegradable polymers include poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), and poly(methacrylic acid). Biodegradable polymers particularly preferred in the present invention include polylactides (PLA), polyglycolides (PGA), poly(lactide-co-glycolides) (PLGA), polyanhydrides, polycaprolactone, poly-3-hydroxybutyrate and polyorthoesters. Such biodegradable polymers have been characterized extensively and can be formulated to exhibit desired degradation properties as (see, e.g., Edlund & Albertsson, Degradable Aliphatic Polyesters, pp. 67-112 (2002), Barman et al., J. of Controlled Release 69:337-344 (2000); Cohen et al., Pharmaceutical Res. (8): 713-720 (1991)). Degradation and drug release kinetics can be precisely controlled by the physicochemical properties of the polymer, such as molecular weight, dispersity index, hydrophobicity, and crystallinity. In general, therapeutics can be released in a controlled manner with first-order kinetics due to drug diffusion through the polymeric matrix or triggered in response to the local environment. The nanoparticle surface may be sterically stabilized by grafting, conjugating, or adsorbing hydrophilic polymers such as PEG to its surface, which can also reduce hepatic uptake and improve circulation half-life.

In one particular embodiment, the polymer comprises poly(lactide-co-glycolides) (PLGA)-PEG. PLGA is a copolymer which has been used in a host of FDA approved therapeutic devices, owing to its biodegradability and biocompatibility. During polymerization, successive monomeric units of glycolic or lactic acid are linked together in PLGA by ester linkages, thus yielding a linear, aliphatic polyester as a product.

Depending on the ratio of lactide to glycolide used for the polymerization, different forms of PLGA can be obtained: these are usually identified in regard to the monomers' ratio used (e.g., PLGA 75:25 identifies a copolymer whose composition is 75% lactic acid and 25% glycolic acid). PLGA degrades by hydrolysis of its ester linkages in the presence of water. It has been shown that the time required for degradation of PLGA is related to the monomers' ratio used in production: the higher the content of glycolide units, the lower the time required for degradation. An exception to this rule is the copolymer with 50:50 monomer ratio which exhibits a faster degradation (about two months). In addition, polymers that are end-capped with esters (as opposed to the free carboxylic acid) demonstrate longer degradation half-lives. The vaccine may be encapsulated in batches of nanoparticles having different release profile. In such embodiments, a single type of biodegradable polymer may be used, but used in formulations with different release profiles; alternatively, different biodegradable polymers having different release characteristics may be used.

Methods of Use

In the methods disclosed herein, an immunologically effective amount of a vaccine composition comprising an adjuvant of the disclosure, as described herein, is administered to a patient in a manner effective to result in an immune response to antigens present in the vaccine. The timing of doses depends upon factors well known in the art. After the initial administration one or more booster doses may subsequently be administered to maintain antibody titers and efficacy of cell-mediated immunity. An example of a dosing regimen would be a dose on day 1, a second dose at from 2 weeks, 3 weeks, 4 weeks, 5 weeks, 6 weeks, 7 weeks, 8 weeks, 9 weeks, 10 weeks or more, a third dose at either 4, 6 or 12 months, and additional booster doses at distant times as needed.

In one aspect, the invention provides a means for monitoring the immune response to vaccine, e.g., 9 to 15 weeks after administration of the vaccine; by measuring the level of antibodies or responsive T cells against the antigen of the vaccine. Vaccines may also be monitored by testing the recipient for expression of cytokines, e.g. toxicity may be monitored by measuring the expression of cytokines produced in response to immunization with a vaccine relative to a reference adjuvant where the adjuvant of the disclosure results in relatively lower levels of one or more cytokines such as, e.g. IFNα, CXCL1 (groA), MIP1A, Rantes, IL-17A, IL-31, IL-6, IP-10, MCP1, MIP1B, etc. The serum levels of such one or more cytokines may be reduced by at least 10%, at least 25%, at least 50%, at least 75% or more relative to the levels produced by the free TLR adjuvant, or by a conventional alum adjuvant.

The vaccine formulations may be used in immunization for various infectious diseases. In some embodiments, the recipient is infected or at risk of microbial infection.

The vaccine formulation is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the vaccine formulation is suitably administered by pulse infusion, particularly with declining doses of the vaccine.

For the prevention of disease, the appropriate dosage of vaccine will depend on the type of disease to be treated, the severity and course of the disease, whether the vaccine is administered for preventive purposes, previous therapy, the patient's clinical history and response to the vaccine, and the discretion of the attending physician. The vaccine is suitably administered to the patient at one time or over a series of treatments.

In another embodiment of the invention, an article of manufacture containing materials useful for the vaccination described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is one or more antibodies in a formulation of the invention as described above. The label on, or associated with, the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

Therapeutic formulations are prepared for storage by mixing the vaccine having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The vaccine composition will be formulated, dosed, and administered in a fashion consistent with good medical practice. The "therapeutically effective amount" of the vaccine to be administered will be governed by clinical considerations, and is the minimum amount necessary to reduce virus titer in an infected individual.

One may adjust dosage based on the amount of peptide delivered. An immunologically effective dose is one that stimulates the immune system of the patient to establish a level immunological memory sufficient to provide long term protection against disease caused by infection. More precise dosages should be determined by assessing the immunogenicity of the vaccine produced so that an immunologically effective dose is delivered.

The therapeutic dose of adjuvant may be at least about 0.01 μg/kg body weight, at least about 0.05 μg/kg body weight; at least about 0.1 μg/kg body weight, at least about 0.5 μg/kg body weight, at least about 1 μg/kg body weight, at least about 2.5 μg/kg body weight, at least about 5 μg/kg body weight, and not more than about 100 μg/kg body weight. It will be understood by one of skill in the art that such guidelines will be adjusted for the molecular weight of the active agent, e.g. in the use of vaccine fragments, or in the use of vaccine conjugates. The dosage may also be varied for localized administration, or for systemic administration, e.g. i.m., i.p., i.v., and the like.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The invention now being fully described, it will be apparent to one of ordinary skill in the art that various changes and modifications can be made without departing from the spirit or scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all of the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1

A Novel Toll-Like Receptor 7-Agonist-Nanoparticle Vaccine Adjuvant Promotes Both Humoral and Cellular Immune Response In this invention, we have developed a novel TLR7 agonist-nanoparticle (NP)-based vaccine adjuvant. By uniquely integrating the well-established ring-opening polymerization (ROP) into the formulation of NPs, we successfully demonstrated the feasibility of facile large-scale production of highly biocompatible TLR7 agonist-based nanoparticle adjuvant with well-controlled physicochemical properties including sub-100 nm size, very narrow size distributions, predefined drug loading, precisely defined composition, and tunable drug release kinetics. With these optimal physicochemical properties, this adjuvant system improves in vivo retention, draining lymph node (LN) accumulation, and cellular uptake of TLR7 agonist by various antigen-presenting cells, leading to persistent mobilization and activation of dendritic cells and cells of monocytic lineage in draining LNs. The constant activation of innate immune cells leads to subsequent early and robust induction of T follicular helper cells response, which boosts early geminal center response to control antigen-specific antibody production. In addition to humoral responses, this TLR7 agonist-NP efficiently promotes a potent CD8 T cell response in draining LNs and lung tissues.

We further demonstrate the wide applications of this TLR7 agonist-NP as a universal adjuvant to multiple vaccine platforms including influenza vaccine and SARS-CoV-2 vaccine. In combination with one recombinant hemagglutinin (HA) strain of influenza viruses, this TLR7 agonist-NP adjuvanted influenza vaccine rapidly and efficiently induces high-level cross-reactive antibody responses to multiple strains from different HA subtypes. Most importantly, it induces early and marked improved titers of cross-reactive HA stalk-specific antibodies, which are often considered the key to developing the universal flu vaccine. As a result, this this TLR7 agonist-NP adjuvanted influenza vaccine generates effective cross-protection against the heterosubtypic H1N1 viruses. Interestingly, when combining with full-length spike protein of SARS-CoV-2 viruses, this TLR7 agonist-NP adjuvanted vaccine not only induced the high-level antibody response against the receptor binding domain (RBD) from the original spike protein, but also marked enhanced the antibodies against certain variants from the U.K., the South Africa and the Brazil lineages, compared to the conventional alum-adjuvanted vaccine.

Finally, we assessed the translation capability of this TLR7 agonist-NP adjuvant from mouse to human. Leveraging the recently developed a tonsil organoid system using discarded human tonsil cells from sleep apnea patients, we demonstrated this TLR7 agonist-NP adjuvanted vaccine significantly enhances the adaptive immune responses against SARS-CoV-2 viruses, including the robust B-cell differentiation and the generation of antibodies specific for SARS-CoV-2 spike protein.

Results and Discussion

Figure 1B:
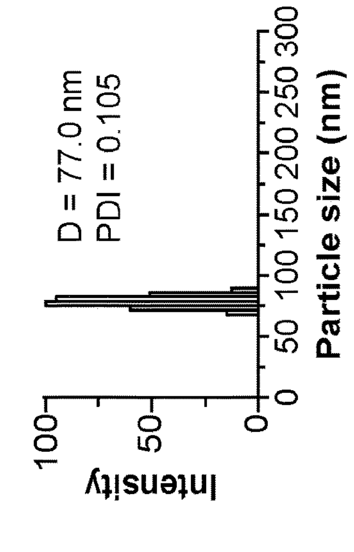

Synthesis and characterization of gardiquimod-polylactide nanoparticles (TLR7-NPs). The TLR7-NPs were constructed through co-nanoprecipitation of TLR7-PLA polymer conjugates and poly(ethylene glycol)-b-poly(lactic-co-glycolic acid) (PEG-PLGA) (FIG. 1*a*). TLR7-PLA polymer conjugates were synthesized by using gardiquimod, a potent agonist for TLR7 receptor expressed in both mouse and human, to initiate the ring-opening polymerization (ROP) of lactide. This method allowed for quantitative incorporation of gardiquimod into PLA polymers and resulted in TLR7-PLA conjugates with precisely controlled composition and molecular weights. At a monomer/initiator (LA/gardiquimod) ratio of 25, gardiquimod loading was achieved as high as 14.8 wt % with nearly 100% incorporation efficiency. The resultant TLR7-PLA polymer conjugates were then mixed with PEG-PLGA in dimethylformamide (DMF) followed by nanoprecipitation into rapidly stirred water to self-assemble into TLR7-NPs with 77 nm hydrodynamic diameter and narrow size distributions (polydispersity index=0.105) characterized by dynamic light scattering (DLS) (FIG. 1*b*).

Figure 1C:
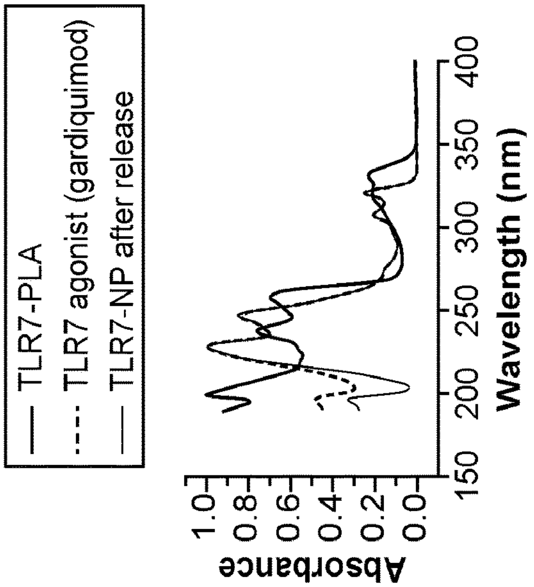
Figure 1D:
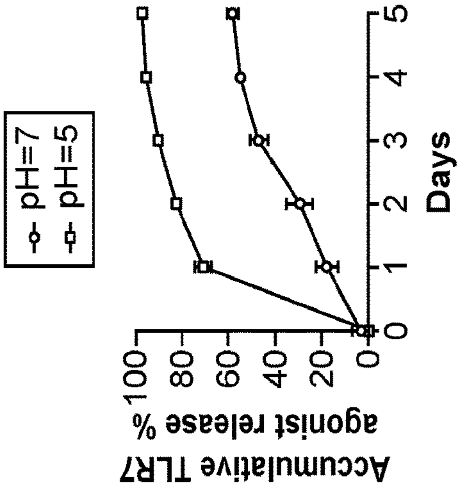

In the design of TLR7-NPs, gardiquimod was conjugated to PLA polymer through ester linkages and could be released from NPs subjected to hydrolysis of ester bonds in the physiological condition. Released gardiquimod from TLR7-NPs (red) shared the identical UV-vis absorbance spectrum as the original gardiquimod compound (black) providing the evidence of releasing unmodified TLR7 agonist without any residual chemical groups (FIG. 1*c*). To mimic the release profile of gardiquimod from TLR7-NPs in the body, we next conduct the kinetic studies of TLR7-NPs at different pH 5.0 and 7.4. Consistent with expectations, gardiquimod was release from NPs in a sustained manner without burst release effects, potentially minimizing the undesired systemic toxicities during the circulation; the release rate of gardiquimod from NPs was accelerated at increased acidities, likely due to faster hydrolysis at lower pH, which is important for robust activation of the intracellular TLR7 receptors once NPs are internalized into cells (FIG. 1*d*).

Figure 2A:
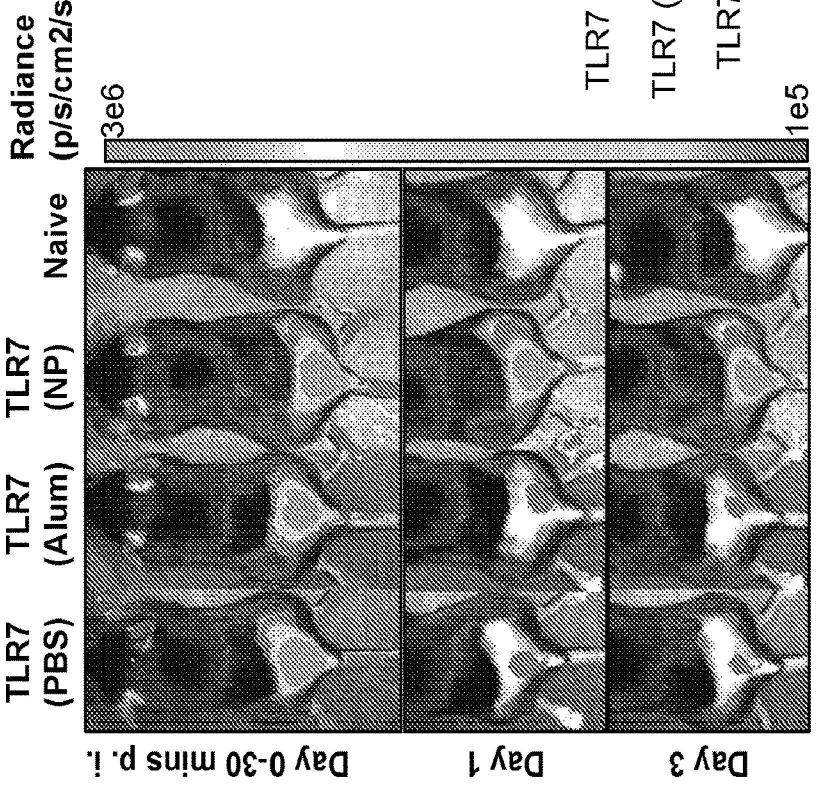
FIGS. 2A-2E. TLR7-NPs improve in vivo retention, draining LN accumulation, and cellular uptake of TLR7 agonist by antigen presenting cells, leading to persistent mobilization of DCs and cells of monocytic lineage in draining LNs. (a) AF647 fluorophore-labeled gardiquimod (20 nmol) was dissolved in PBS (TLR7 (PBS)), adsorbed on Alhydrogel (TLR7 (alum)), or self-assembled into nanoparticles (TLR7 (NP)), and injected s.c. in C57BL/6 mice (n=4 mice per group from two independent experiments) followed by longitudinal whole-animal in vivo Lago spectral imaging system. Shown are representative images of one mouse from each group and average normalized total radiance from groups of mice at the injection site over time. (b) Lago fluorescence imaging of excised draining LNs from C57BL/6 mice (n=4 mice per group from two independent experiments) at Day 1 and Day 3 post administration. Shown are two representative LN images and total radiance of four LNs from one representative experiment. (c) C57BL/6 mice (n=6 mice per group from two independent experiments) were immunized with AF647 labeled TLR7 (PBS), TLR7 (alum), or TLR7 (NP) by s.c. injection, and flow cytometry was performed on the draining LNs at Day 1 and Day 3 post immunization. (b) and (c) Bar graphs represent means±SD, respectively. (d) C57BL/6 mice (n=8-10 from two independent experiments) were immunized with NP-OVA (50 μg) plus TLR7 agonist (20 μg) in three different platforms (PBS, Alum, or NP) on Day 0. Different types of innate immune cells were analyzed by flow cytometry for Day 0 (naïve mice) and Day 1 and 4 post immunization. Data are means±SEM. (e) C57BL/6 mice (n=3-5) were immunized with NP-OVA (50 μg) plus TLR7 agonist (20 μg) in three different platforms (PBS, Alum, or NP) on Day 0. The mean fluorescence intensity (MFI) of CD86 expression on cDC1 and cDC2 were analyzed by flow cytometry for Day 1 and 4 post immunization. Data are analyzed by means±SEM.
Figure 2B:
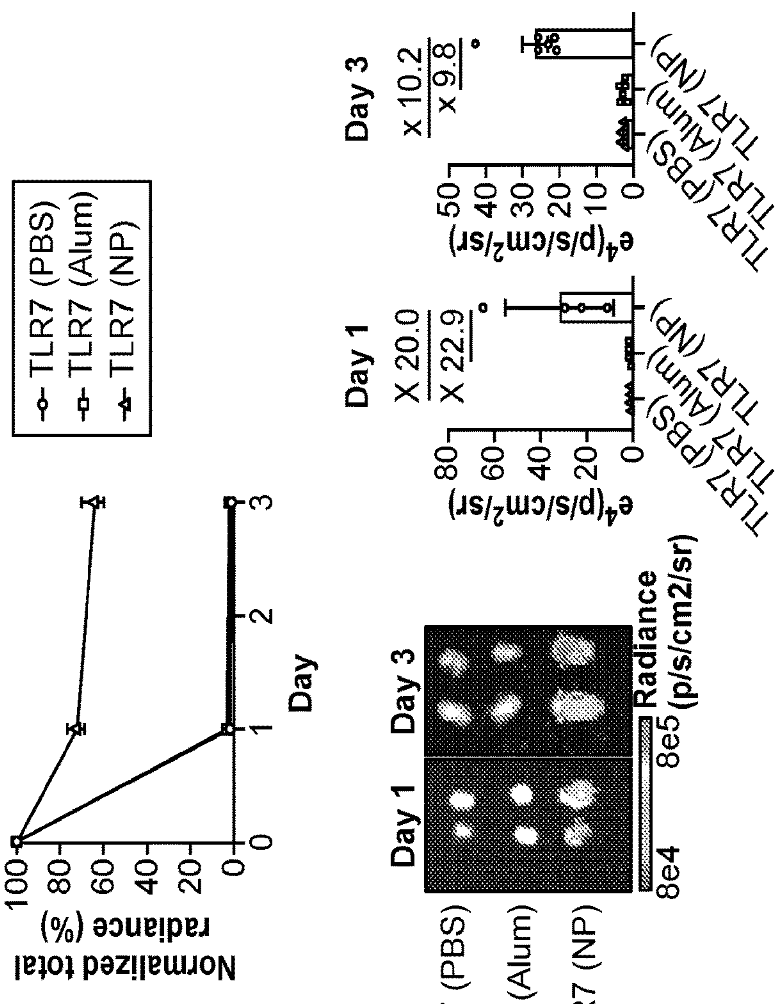

In vivo retention, lymph node trafficking and cellular internalization of TLR7-NPs. To determine how TLR7-NPs influence the in vivo adjuvant performance, gardiquimod in the TLR7-PLA was labeled with AlexaFluor647 (AF647)

and co-nanoprecipitate with PEG-PLGA to formulate into NPs. As comparisons, garduimod dispersed in PBS or adsorbed on alum were also conjugated with AF647, respectively. All three AF647-labeled adjuvants combined with OVA antigen were injected into C57bL/6 mice, and the fluorescence of AF647 at the injection site was tracked by whole-animal fluorescence imaging. Both gardiquimod dispersed in PBS and adsorbed to alum, termed as TLR7 (PBS) and TLR7 (Alum), respectively, were rapidly cleared from injection site only 1 day post injection (p.i.), whereas gardiquimod in the TLR7-NPs, termed as TLR7 (NP), persisted for over 3 days (FIG. 2*a*). Draining lymph nodes (dLNs) were dissected at 1 day and 3 days p.i. to evaluate the accumulation of gardiquimod through measuring the fluorescence intensity of AF647. As shown in FIG. 2*b*, the fluorescence intensity in the draining lymph nodes were significantly enhanced with TLR7 (NP) as early as 1 day p.i., and the increased fluorescence intensity was maintained as long as 3 days p.i., suggesting TLR7 (NP) were preferentially targeted and retained in the draining lymph nodes. In contrast, the accumulation of TLR (PBS) or TLR7 (Alum) in dLNs were much lower than TLR7 (NP) (20-fold decrease at 1 day p.i. and 10-fold decrease at 3 days p.i.).

Figure 2C:
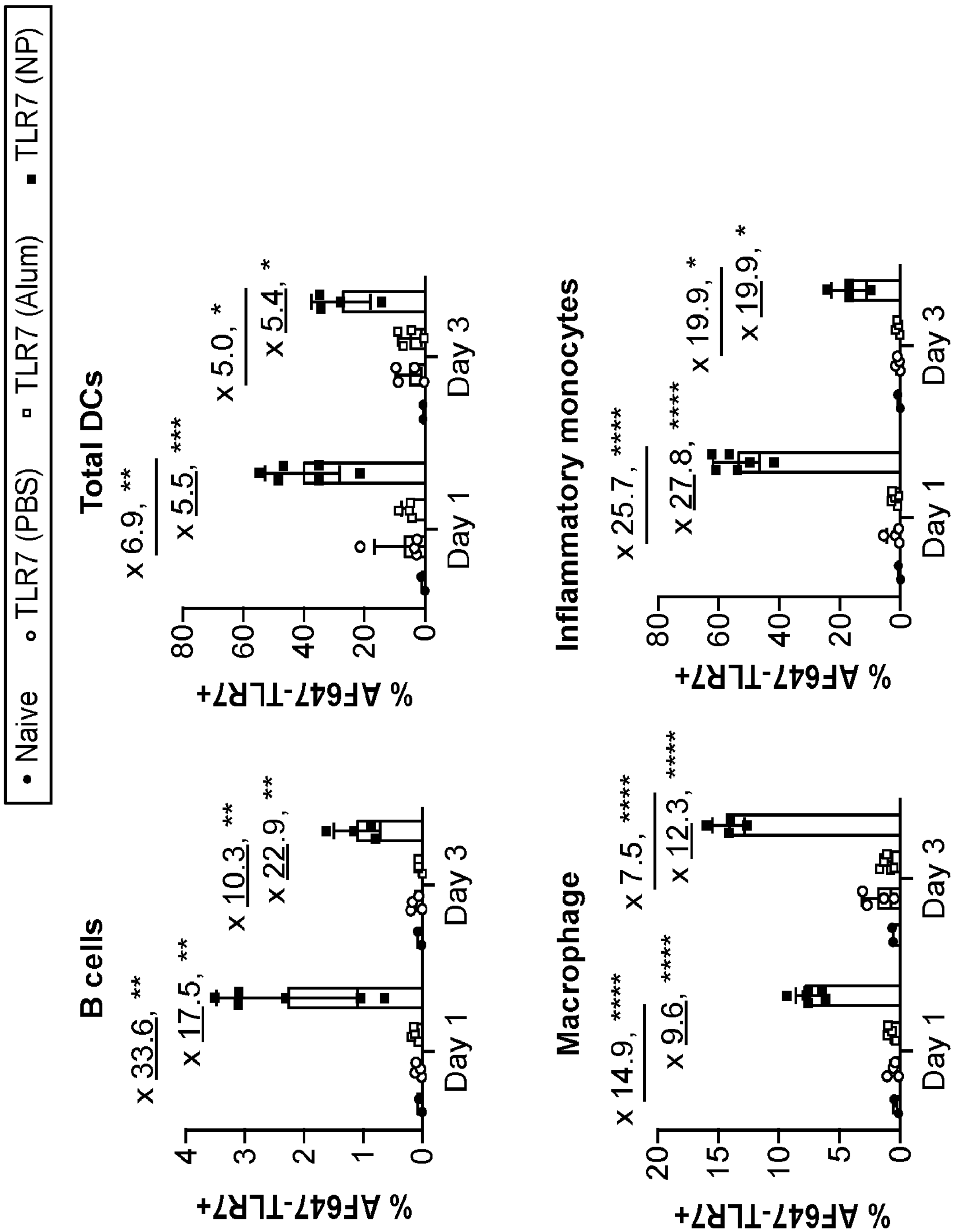
Figure 2D:
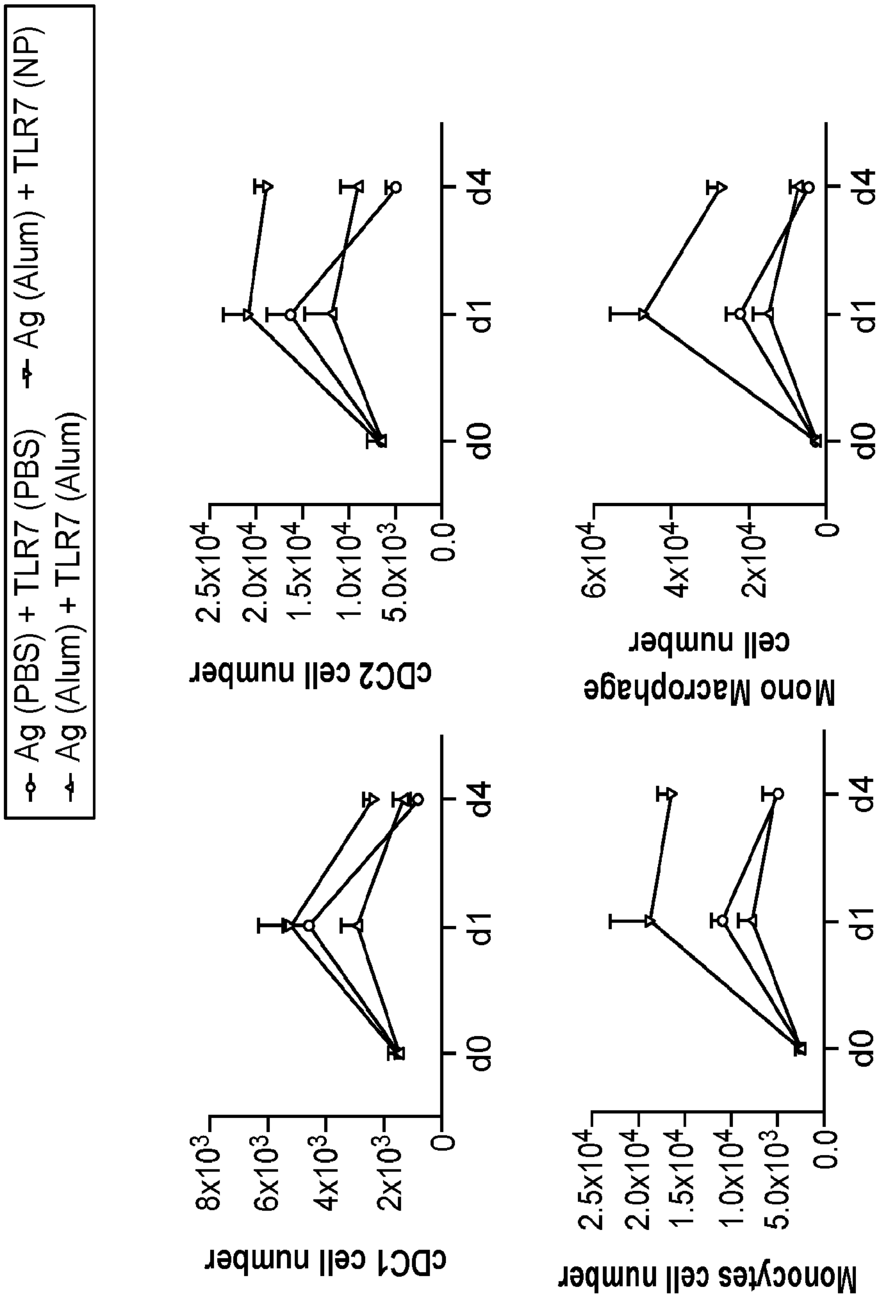

Given the preferential in vivo retention and the enhanced LN targeting of TLR7 (NP), we next sought to evaluate how TLR7-NPs impact the cellular internalization of gardiquimod at single cell level using flow cytometry. Strikingly, there was a 5.5 to 33.6-fold increase in the cellular uptake of TLR7(NP) in the vast majority of antigen-presenting cells (APCs) in dLNs, including B cells, total DCs, macrophages, and inflammatory monocytes, compared to that of TLR7 (PBS) or TLR7 (Alum) as early as 1 day p.i. This enhanced cellular uptake of TLR7 (NP) in various APCs remained at a high level as long as 3 days p.i., with a 5.5 to 20.9-fold increase than that of TLR7 (PBS) or TLR7 (Alum) (FIG. 2*c*). Interestingly, this persistent adjuvant capture of APCs leads to potent and persistent mobilization of DCs and cells of monocytic lineage in dLNs (FIG. 2*d*).

Figure 2E:
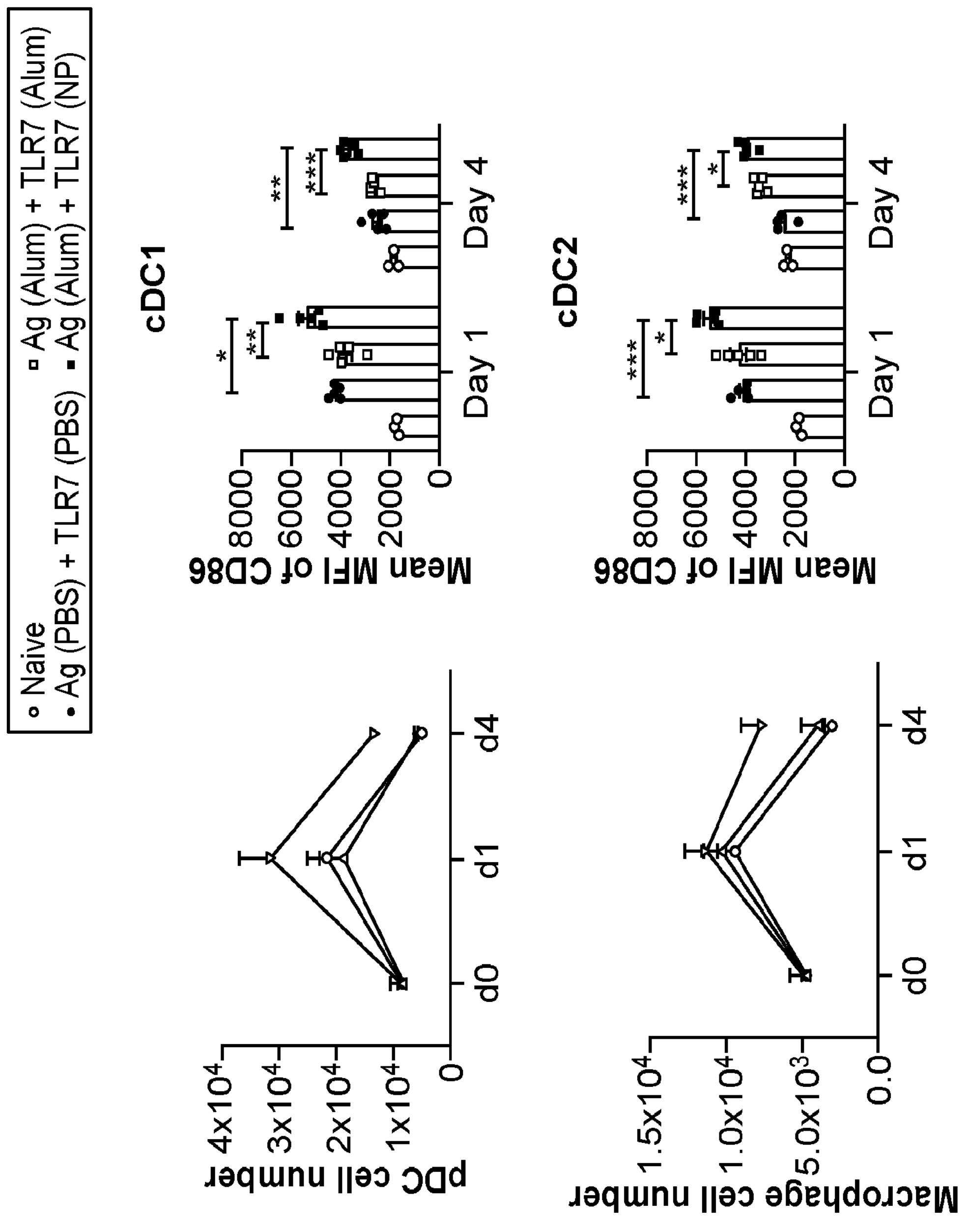
Figure 3A:
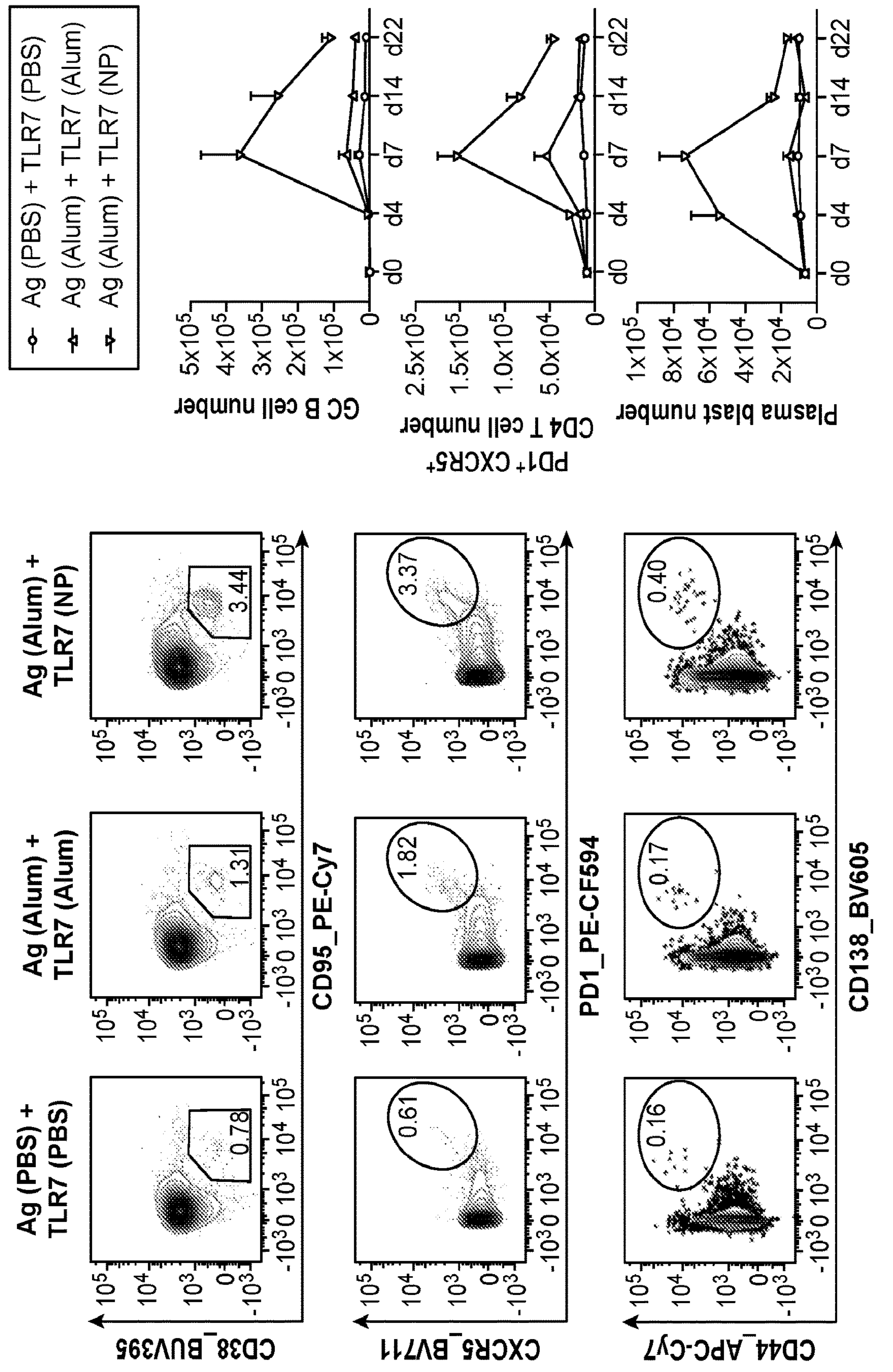
FIGS. 3A-3B. TLR7-NPs adjuvanted vaccine enhances GC and early plasma blast responses. C57BL/6 mice were immunized with NP-OVA (50 μg) plus TLR7 agonist (20 μg) in three different platforms (PBS, Alum, or NP) on Day 0. (a) GC B cells, follicular CD4 T cell ($CD4^+CXCR5^+PD1^+$) and plasma blasts in the draining LNs were analyzed by flow cytometry. Shown are representative flow cytometry plots of LN samples on Day 7 (left) and the cell number quantification of LN samples from Day 4, 7, 14 and 22. Data represent 6-8 mice from 2-3 independent experiments. (b) Follicular T cells ($BCL6^{hi}$ $PD1^{hi}$) were analyzed for Tfr ($FOXP3^+$) on Day 7. Data represent 6-9 mice from 2 independent experiments. All the data are means±SEM.
Figure 3B:
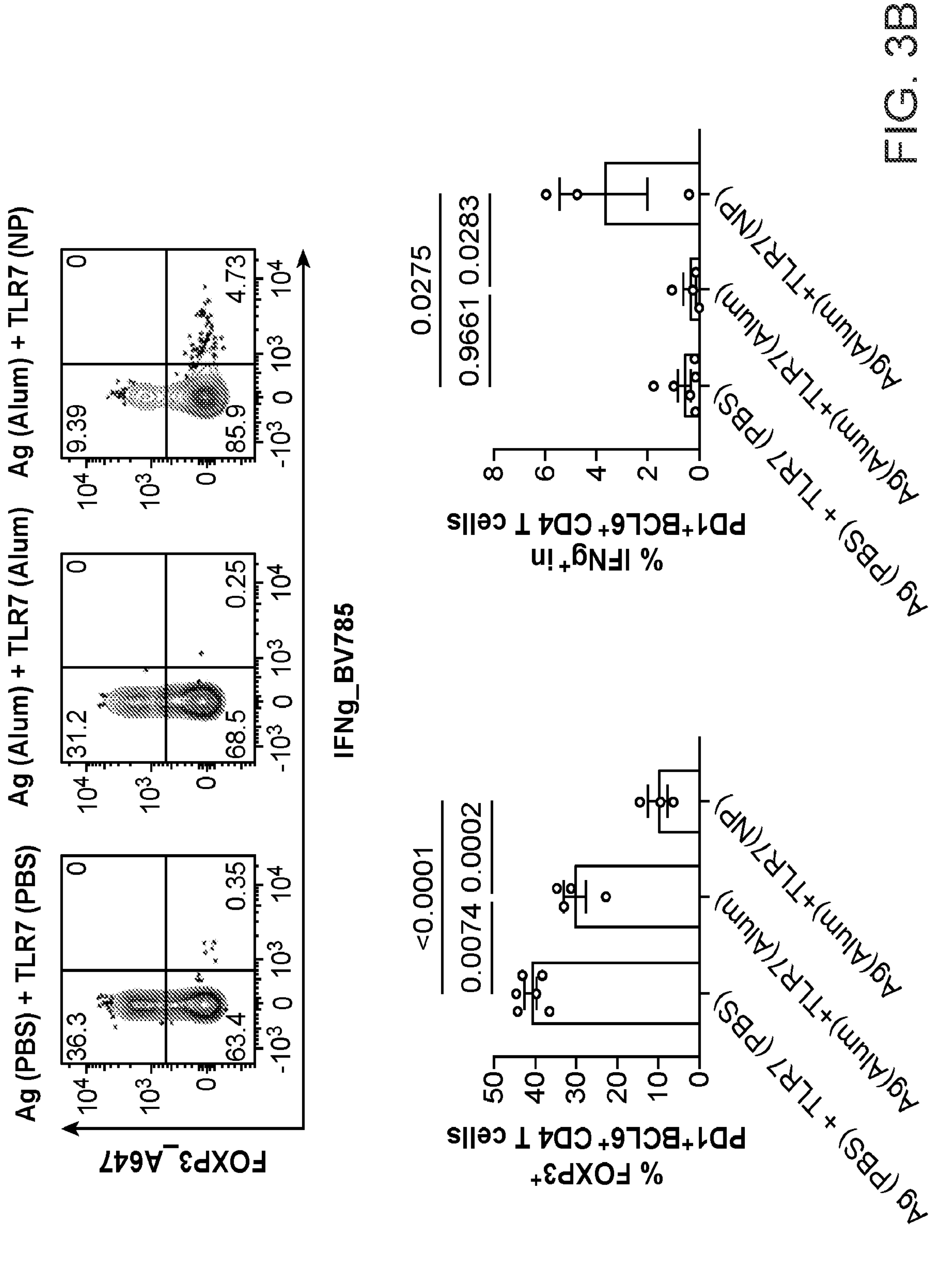

TLR7-NPs adjuvanted vaccine promotes the persistent activation of DCs in draining LNs. Interestingly, the persistent adjuvant capture of APCs leads to potent and persistent mobilization of DCs in dLNs (FIG. 2*d*) as well as their activation, characterized by CD86 expression (FIG. 2*e*).

TLR7-NP potently promote both GC and extrafollicular B cell responses. The enhanced and sustained activation of innate immune cells by TLR7-NP inspired us to look into the adaptive immune response, which is closely linked to innate immunity. Germinal center (GC) reaction plays a central role in determining the vaccine efficacy, leading to high-affinity antibody generation and durable B cell memory formation. To test if TLR7-NPs adjuvant might alter GC reaction, three groups of mice received an equivalent dose of NP-OVA and TLR7 agonist in three different vaccine formulations: group 1 mice were immunized with NP-OVA and TLR7 agonist both in PBS (Ag(PBS)+TLR7(PBS)); group 2 mice were immunized with NP-OVA and TLR7 agonist in Alum (Ag (Alum)+TLR7(Alum)); and group 3 were immunized a simple mix of NP-OVA in Alum and nanoparticle formulation TLR7 agonist (Ag(Alum)+TLR7(NP)). We then did a time course study from day 4 to day 22 p.i. We started to detect GC B cells on day 7 in the draining LNs from Ag(Alum)+TLR7(NP) immunized mice, and their number was drastically higher than that Alum and PBS groups. Despite that GC B cell number decreased after the peak on day 7, this trend lasted to the latest we have tested (day 22).

In fact, day 22 GC B cell numbers in Ag(Alum)+TLR7(NP) group were still higher than peak GC B cell numbers in the other groups.

GC selection relies on B-T cell interaction, in which T cells provide essential help to support GC B cells survival and selection. Consistent with GC B cell numbers, follicular T cells expressing CXCR5 and PD1 were also highly expended in Ag(Alum)+TLR7(NP) group. Follicular T cells include T follicular helper cell (Tfh) and T follicular regulatory cell (Tfr). Tfhs are the real helper cells to promote GC response, while Tfrs express regulatory T cell marker FoxP3 and function to restrain GC reaction. To identify the composition, we first gated on total follicular T cells (BCL6+ PD1+) and further separate into different subsets based on FoxP3 and IFNg expression. Strikingly, there were ~30-40% of follicular T cells on day 7 from PBS or Alum group expressing FoxP3 (defined as Tfr). In Ag(Alum)+TLR7(NP) group, the percentage of Tfr dropped significantly to ~10%. On the other hand, in Ag(Alum)+TLR7(NP) group, there were more cells expressing IFNg, which is a Th1 cytokine that can promote B cells switching. All these data highly suggest nanoparticle formulation is very potent in promoting GC response. Interestingly, TLR7-NP could also promote extrafollicular B cell response as we found more early plasma cells in Ag(Alum)+TLR7(NP) group compared to other groups. Extrafollicular B cell response is important in generating early antibody mediated protection.

Figure 4A:
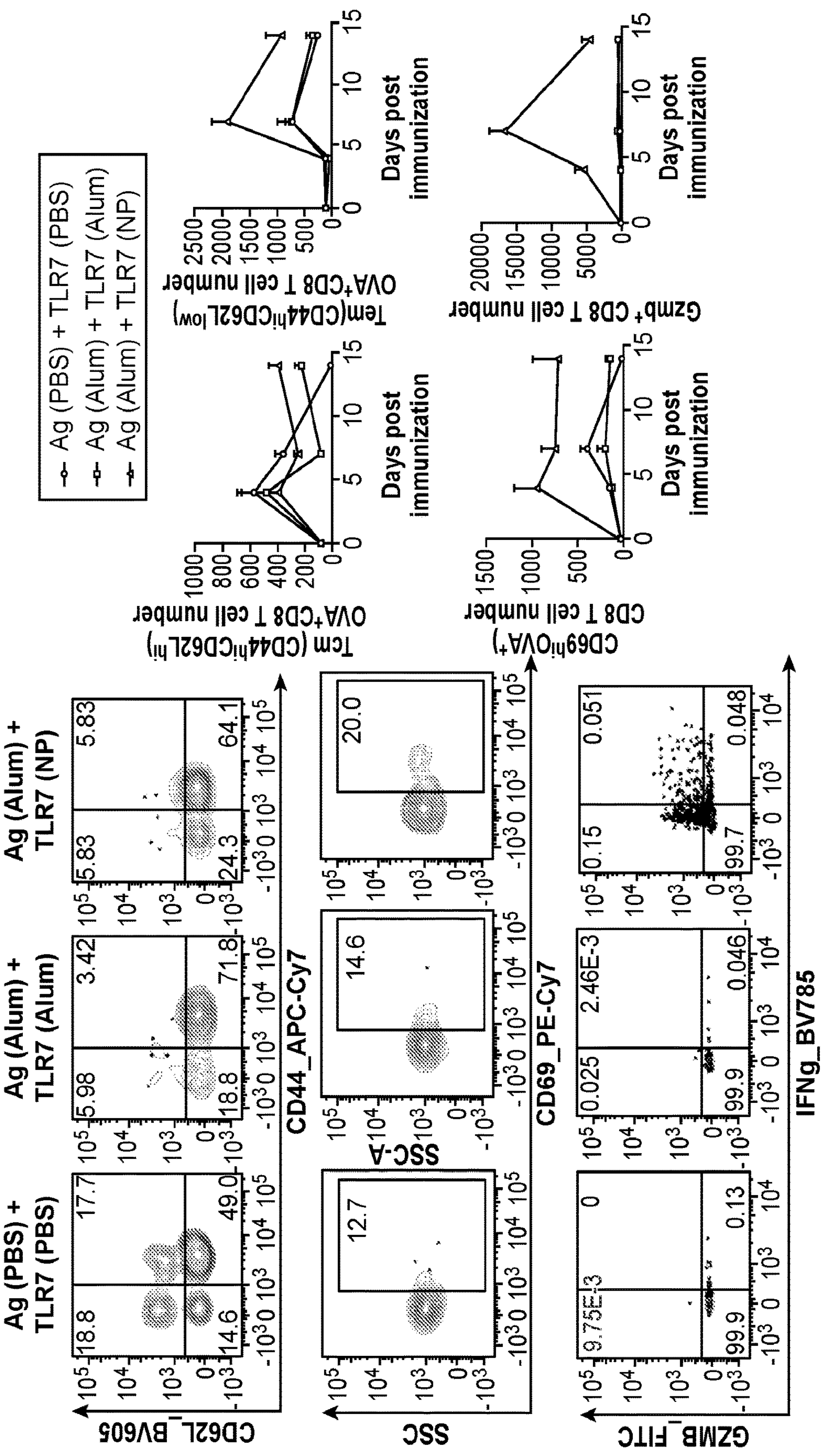
FIGS. 4A-4B. TLR7-NPs adjuvanted vaccine elicits a robust antigen-specific $CD8^+$ T cell response in both draining LNs and lungs. (a) C57BL/6 mice (n=4-6 per group) were immunized with NP-OVA (50 μg) plus TLR7 agonist (20 μg) in three different platforms on Day 0. Shown are representative flow cytometry plots (left) and the corresponding quantification (right) of tetramer-positive central memory ($CD44^{hi}CD62L^{hi}OVA^{+}$) $CD8^{+}$ T cells, tetramer-positive effector memory ($CD44^{hi}CD62L^{low}OVA^{+}$) $CD8^{+}$ T cells, tetramer-positive activated ($CD69^{hi}OVA^{+}$) $CD8^{+}$ T cells, and functional $CD8^{+}$ T cells producing Gzmb in draining LNs on Day 4, 7 and 14. (b) C57BL/6 mice (n=4 per group) were immunized with NP-OVA (50 μg) plus TLR7 agonist (20 μg) in three different platforms on Day 0. Shown are representative flow cytometry plots (left) and the corresponding quantification (right) of tetramer-positive effector memory ($CD44^{hi}CD62L^{low}OVA^{+}$) $CD8^{+}$ T cells and functional $CD8^{+}$ T cells producing Gzmb in the lung on Day 14. All the data are means±SEM.

TLR7-NPs adjuvanted vaccine elicits a robust antigen-specific $CD8^+$ T cell response. TLR7-NPs has efficiently induced persistent mobilization and activation of cDC1, which have been shown vital for cross-priming CD8 T cells. We then sought to determine if TLR7-NP adjuvanted vaccination also enhanced antigen-specific $CD8^+$ T cell response, as they are critical for controlling virus infection. As FIG. 4*a* showed, there was a marked enhancement in the number of effector memory (CD44hiCD62Llow) OVA-specific $CD8^+$ T cells in dLNs 7- and 14-days post Tpost immunization of NP-OVA(Alum)+TLR7(NP) (FIG. 4*a*). The proportion of $CD69^{hi}$+$CD8^+$ cells rose significantly 4 days and persists until 14 days p.i. indicating the early and persistent activation of OVA-specific $CD8^+$ T cells in response to TLR7-NPs adjuvanted vaccination (FIG. 4*a*). Further, flow cytometry analysis showed TLR7-NP adjuvanted vaccine efficiently induces granzyme B (Gzmb) producing $CD8^+$ T cells in dLNs. In contrast, two other control adjuvants failed, demonstrating TLR7-NPs not only augment quantity but also quality of cellular immune responses.

Figure 4B:
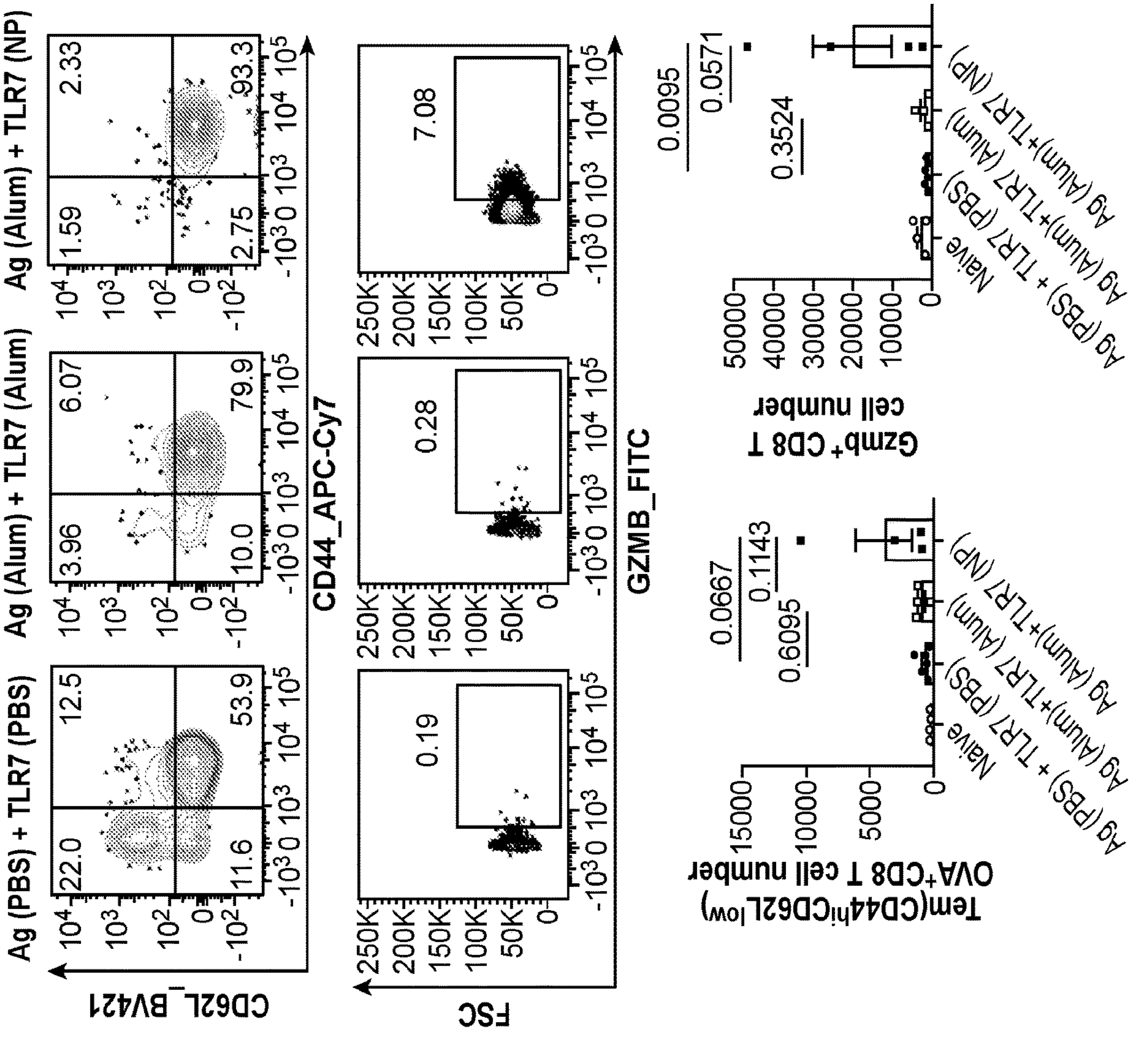

As antigen-specific memory $CD8^+$ T cells capable of rapid recall upon viral infection are critical for controlling viral replication in the lung, we next analyzed the $CD8^+$ T cell responses in the lung after 14 days post immunization. As shown in FIG. 4*b*, TLR7-NPs adjuvants efficiently drove the OVA-specific $CD8^+$ T cells towards effector memory phenotype differentiation compared to the other two adjuvants control. A large number of functional $CD8^+$ T cells expressing Gzmb were observed in the lung after receiving TLR7-NPs adjuvanted NP-OVA vaccine, whereas Gzmb produced $CD8^+$ T cells barely detected in the lungs of mice receiving both TLR7 (PBS) and TLR7 (Alum) adjuvanted vaccines. Altogether, TLR7-NPs were superior to either soluble agonist TLR7 (PBS) or alum-bound agonist TLR7 (Alum) in the induction of potent $CD8^+$ T-cell responses.

Figures 5A, 5B:
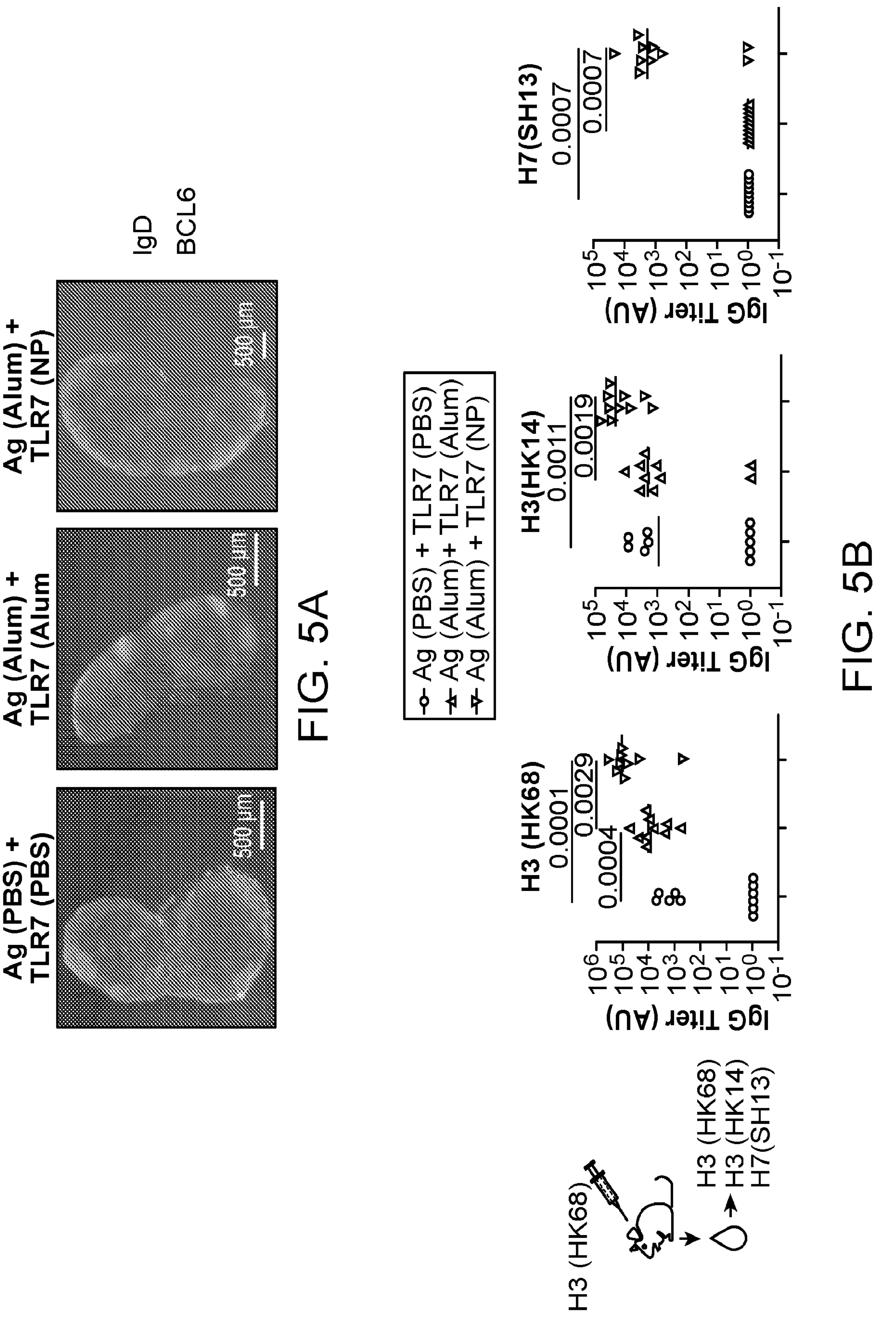
FIGS. 5A-5E. TLR7-NPs adjuvanted HA immunization induces cross-reactive and stem binding antibodies. (a) C57BL/6 mice were immunized with HA of H1 N1 A/Puerto Rico/8/34 (PR8 HA, 10 μg) plus TLR7 agonist (20 μg) in three different platforms (PBS, Alum, or NPs) at day 0. GC response in the draining LNs (Day 7) were analyzed by immunofluorescence. B cell zone and GC were stained with IgD and BCL6, respectively. Data show one representative LN imaging from two mice of each group. (b-c) Mice were immunized with HA (10 μg, strain as indicated) plus TLR7 agonist (20 μg) in three different platforms (PBS, Alum, or NPs) on Day 0. Serum samples were collected on Day 14 and analyzed by ELISA for antibodies binding to HAs from homo- and heterologous strains as indicated. (d) Serum from (c) were tested by ELISA for antibodies binding to the stem region of PR8 HA. (e) Mice were immunized with HA of H1N1 A/New Caledonia/20/1999 (NC99, 10 μg) plus TLR7 agonist (20 μg) in three different platforms (PBS, Alum, or NP) on Day 0. Serum samples were collected on Day 14 and analyzed by ELISA for antibodies binding to HA stem region and full-length HA from H1N1 A/Puerto Rico/8/34. All the data are medians with each dot representing one mouse.
Figures 5C, 5D, 5E:
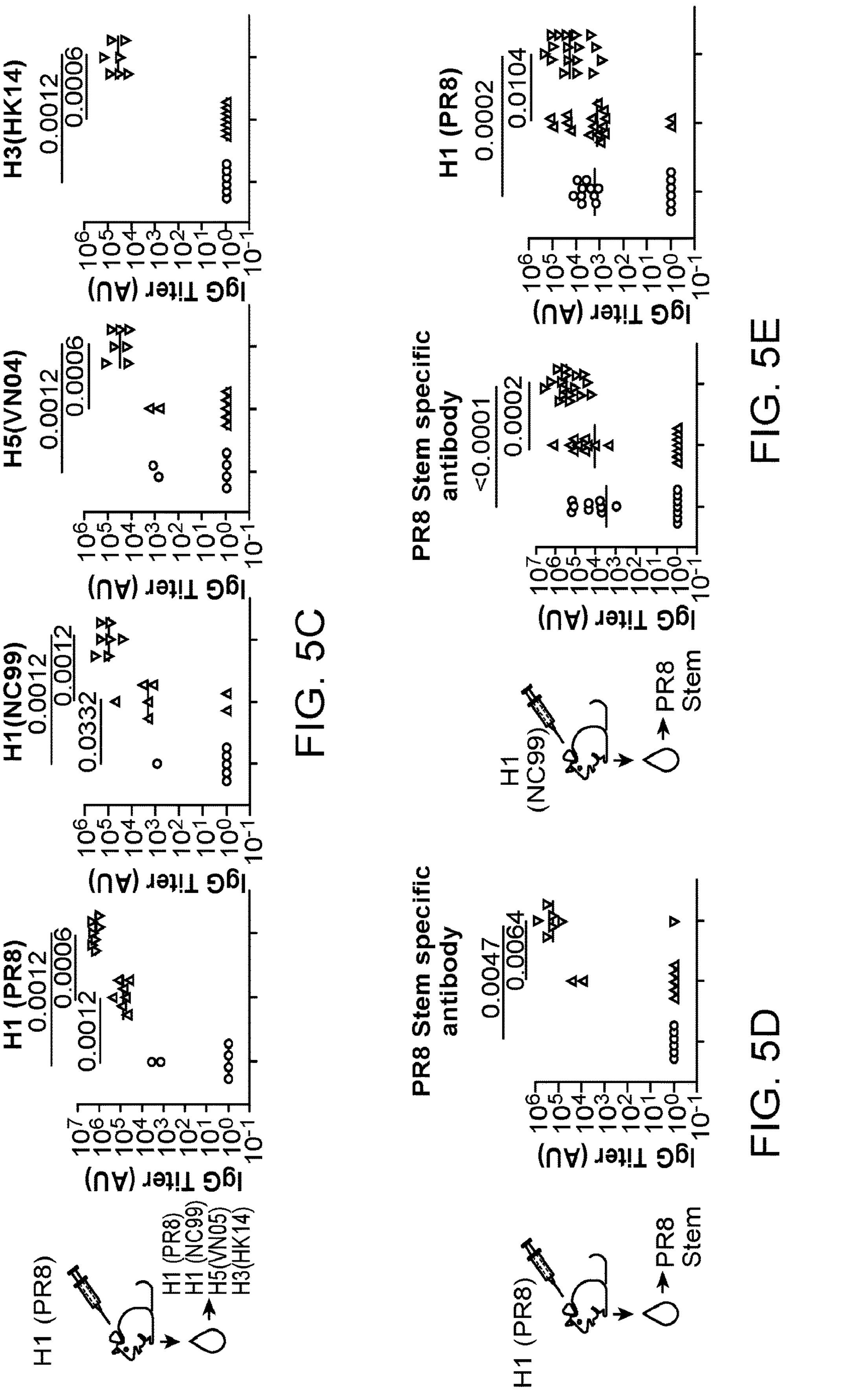

TLR7-NPs adjuvanted HA immunization induces cross-reactive and stem binding antibodies Influenza is a deadly infectious disease and has been a massive threat to human health. However, developing a universal influenza vaccine has been challenging and unsuccessful. The primary reason is immunodominance, in which antibody and memory responses are focused on dominant epitopes where escaping mutations can happen frequently and rapidly. The potent effect of promoting GC response by TLR7-NP adjuvant suggests its potential to tackle this issue. More importantly, TLR7-NP adjuvant can drastically increase the ratio of Tfh to Tfr, which might increase the diversity of B cell clones in GC by providing them more help signals. As such, we hypothesized that TLR7-NP adjuvant might help overcome immunodominance and increase the breadth of antibody response against hemagglutinin (HA). First, we performed the immunofluorescence staining of mice who received the immunization of HA plus TLR7-NPs, and confirmed the dramatically enhanced GC reaction can be observed 7 days p.i. (FIG. 5*a*). Next to test whether TLR7-NPs can promote breadth, we immunized mice with H3 HA from influenza strain A/Hong Kong/1/1968 (HK68), one strain from group 2 in the phylogenetic tree, and did serology for antibodies against HAs from heterologous strains (FIG. 5*b*). The result showed that TLR7-NPs not only increased antibody titers against the immunized H3 HA from HK68, but also enhance antibody responses against H3 HA from a different strain A/Hong Kong/4801/2014 (HK14). More strikingly, most mice immunized with TLR7-NP adjuvanted H3 HA were able to make antibodies against H7 HA, which is from a strain of a different subtype. By contrast, these cross-subtype antibodies could not be detected in the mice immunized with HA adjuvanted by either TLR7(PBS) or TLR7(Alum). To confirm if TLR7-NPs can induce a similar effect with HA from group 1 in the phylogenetic tree, we used H1 HA from PR8 in a similar immunization experiment setting. Again, we found that mice immunized TLR7-NP adjuvanted PR8 HA generated more significant levels of antibodies against HA of cross-subtype or even cross-group (FIG. 5*c*). The head region of HAs from different influenza strains is highly variable and mutable, while the stem region is more conserved. We hypothesized the antibodies against stem might explain such cross-reactivity. To test if TLR7-NP could skew the immunodominance from mutable HA head region to conserved stem region, we did ELISA with headless HA protein. We found that TLR7-NP induced a much greater level of stem-specific antibodies for both PR8 H1 and NC99 H1 HA immunization (FIG. 5*d*). Hence, using three different HAs as the immunogen, we demonstrated the potential of TLR7-NPs as an adjuvant to boost cross-reactive antibody responses for universal influenza vaccines.

Figure 6A:
FIGS. 6A-6E. TLR7-NPs adjuvanted vaccine efficiently elicit HA stem-specific antibodies and induces cross-protection from lethal heterosubtypic influenza virus challenge. (a) Schematic illustration of vaccination and viral challenge schedule: C57BL/6 mice (n=14-16 from two independent experiments) were immunized with H1N1 A/New Caledonia/20/1999 (10 μg) plus TLR7 agonist (20 μg) in three different platforms on Day 0 (Prime) and Day 21 (Boost). Sera were collected at Week 2 (2 weeks post Prime) and Week 5 (2 weeks post Boost) for antibody measurement in serum. Four weeks post second vaccine immunization, mice were infected with heterosubtypic H1 N1 A/Puerto Rico/8/34 virus. (b) Antibodies titers specific for PR8 H1 N1 stems were measured at Week 2 and Week 5. The body weight changes (c) and survival (d) of mice corresponding to those described in (a). (e) Histological examination of the lungs from different groups of mice on Day 14 post infection. Data are representative of at least four mice from each group.
Figure 6B:
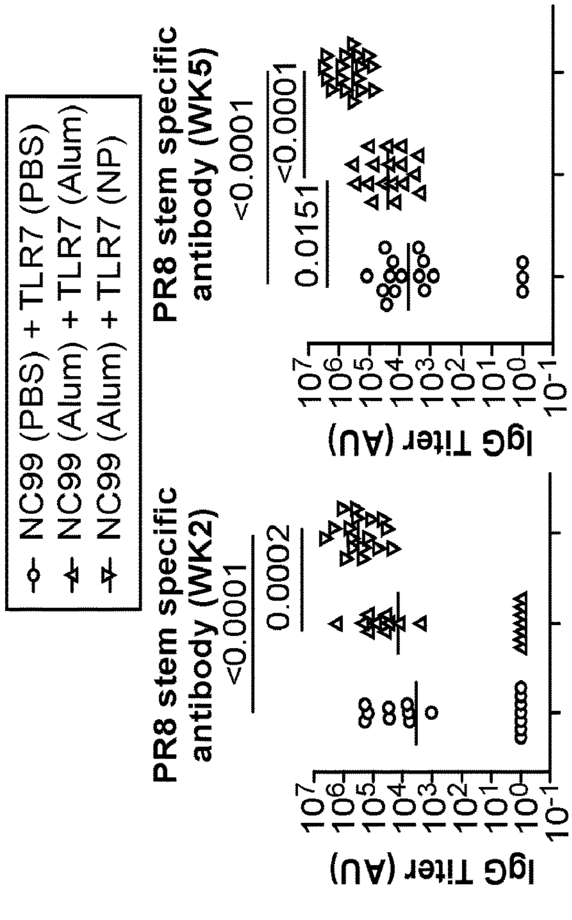

TLR7-NPs adjuvanted HA immunization induces broad protection against heterosubtypic influenza viruses. Given the potent cross-reactive antibody responses have been induced by TLR7-NPs adjuvanted vaccination, we reasoned that TLR7-NPs adjuvant might help generate the cross-protection against different influenza viruses. To evaluate this potential of TLR7-NPs, we immunized mice with three different vaccinations, being TLR7 (PBS)-, TLR7 (Alum)-, and TLR7 (NP) adjuvanted NC99 HA, at week 0 and week 3, respectively. Four weeks post second immunization, mice were challenged with a lethal dose of distinct PR8 H1N1 virus (FIG. 6*a*). Strikingly, TLR7-NPs significantly elevated serum IgG antibodies binding to the conserved, immune subdominant stalk domain on the HA(NC99) in all mice only after primary immunizations (FIG. 6*b*), which is rarely seen in other adjuvants systems.

Figure 6C:
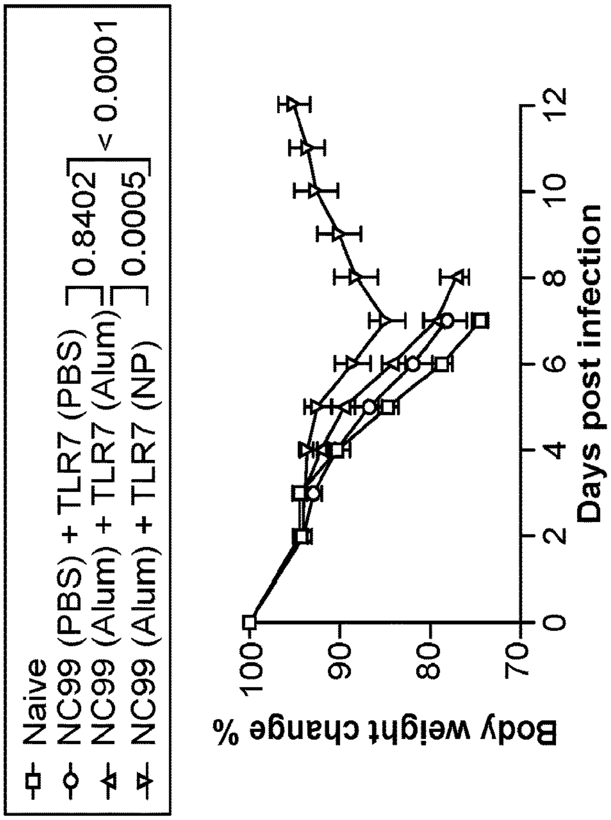
Figure 6D:
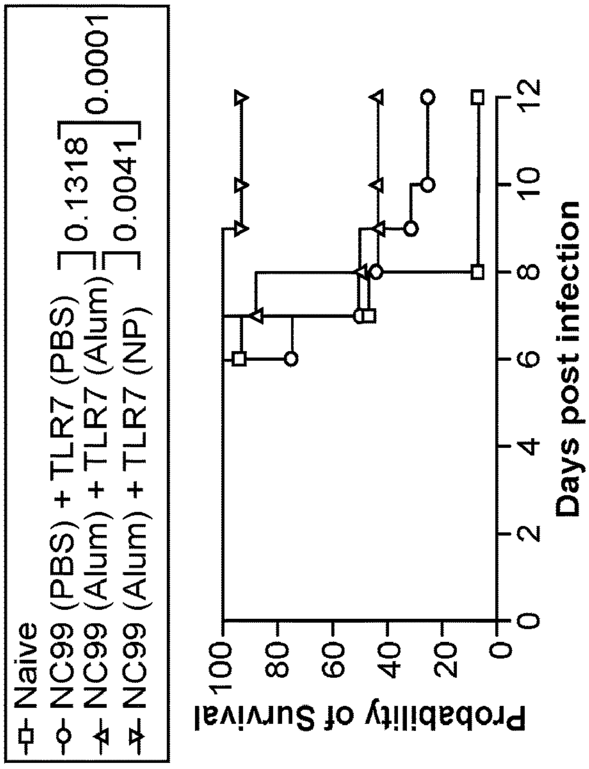
Figure 6E:
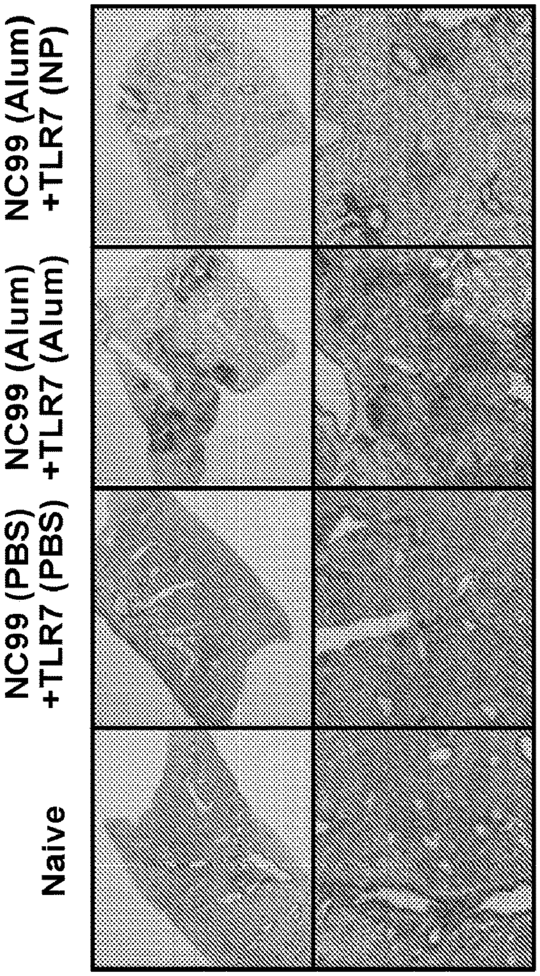

Mice receiving the TLR7-NPs adjuvanted NC99 HA, when challenged with heterosubtypic PR8 H1 N1 virus, showed significantly less body weight loss compared to mice receiving TLR7 (PBS) or TLR7 (Alum) adjuvanted vaccine (FIG. 6*c*). More than 92% of mice recovered their body weight rapidly in the late infection phase (>7 days) (FIG. 6*c*). By contrast, mice received TLR7 (PBS) or TLR7 (Alum) adjuvanted NC99 HA failed to develop protection against lethal challenge with PR8 H1 N1 virus. More than half of mice from these two control groups (75.0% of TLR7 (PBS) adjuvanted vaccine group and 56.25% of TLR7 (Alum) adjuvanted vaccine group) couldn't survive (FIG. 6*d*). Furthermore, we performed the histologic analysis of lung sections from mice survivors 14 days post PR8 H1N1 viral infection. As illustrated in FIG. 6*e*, severe pathologic peribronchiolar inflammation associated with diffuse damage of structures were readily identified within the lung tissues of unvaccinated mice or mice who received TLR7 (PBS) or TLR7 (Alum) adjuvanted vaccines. In contrast, the pulmonary damage was significantly attenuated in mice vaccinated with TLR7-NPs adjuvant and resulted in a trend toward similar normality compared to uninfected mice. This result further supported that TLR7-NPs adjuvanted vaccination could induce enhanced heterologous protection above other treatment groups.

Figure 7A:
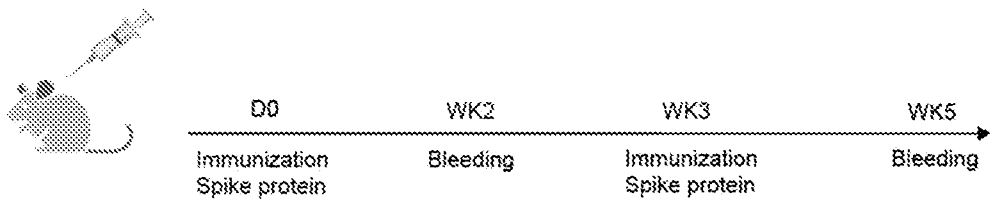
FIGS. 7A-7C. TLR7-NPs adjuvanted spike immunization induces cross-reactive antibodies against the SARS-CoV-2 variant lineages Alpha B.1.1.7, Beta B.1.351, Gamma P.1 Delta B.1.617.2, and Omicron B.1.1.529. (a) C57BL/6 mice (8-10 mice for each group) were immunized with the Alum-adsorbed full-length SARS-CoV-2 Spike protein (5 μg) plus TLR7 agonist (20 μg) in either TLR7-Alum or TLR7-NPs at day 0. Serum samples were collected on Day 14 and Day 35 and analyzed by ELISA for antibodies binding to Spike RBD, Spike S1 and Spike (Wuhan reference strain) (b) and RBD or S1 from variants of all lineages (c). All the data are medians with each dot representing one mouse. Data are analyzed by Mann-Whitney Test. P values are as shown.
Figure 7B:
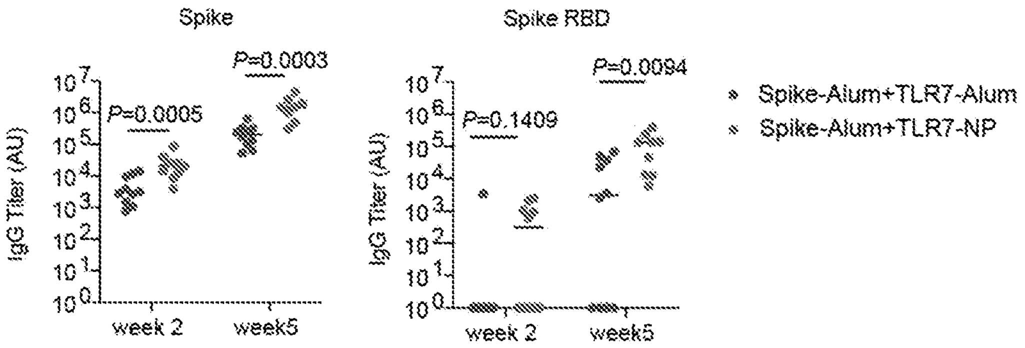
Figure 7C:
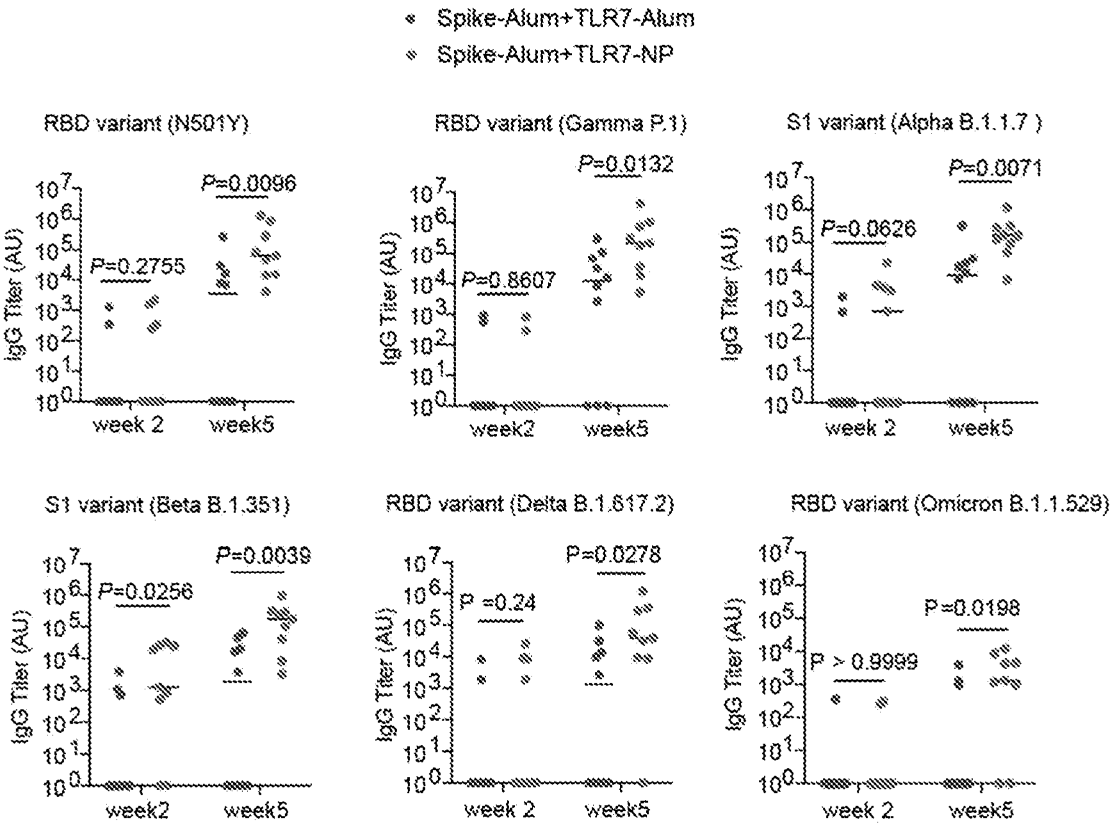

TLR7-NPs adjuvanted spike immunization induces cross-reactive antibodies against the Sars-Cov-2 variant lineages B.1.1.7, B.1.351, P.1, B.1.617.2, and B.1.1.529. The emergence of several SARS-CoV-2 variants of concern with multiple amino acid replacements present in the viral Spike (S) protein and include notable mutations in the receptor binding domain (RBD has implications for the future control of the COVID-19 pandemic). Several of these mutations directly affect ACE2 receptor binding affinity, which may impact infectivity, viral load, or transmissibility. Variants of concern include the Alpha variant B.1.1.7, the Beta variant B.1.351, the Gamma variant P.1, the Delta variant B.1.617.2, and the Omicron variant B.1.1.529. To test if TLR7-NP adjuvant could help increase the breadth of antibody response against these variants of concern, we immunized mice with the full-length spike protein from SARS-CoV-2 virus with TLR7-Alum or TLR7-NP and characterized antibodies in the sera against the wildtype RBD, spike and S1 protein from the above-mentioned variants (FIG. 7). The result showed that all mice received TLR7-NP adjuvanted vaccine not only developed high antibody titers against the immunized spike and RBD at week 5, but also enhance antibody responses against RBD (N501Y) from the multiple lineages, RBD from the Gamma variant lineage P.1, and S1 protein from the Alpha variant lineage B.1.1.7 and the Beta variant lineage B.1.351. By contrast, only 50-60% of TLR7-Alum vaccinated mice developed 2 log titers lower antibody response against either the wildtype RBD or the RBD (N501Y) variants from multiple lineages. Similarly, only 50-60% of TLR7-Alum vaccinated mice developed 2 log titers lower antibody response against S1 variants from the Alpha lineage B.1.1.7 and the Beta lineage B.1.351. Strikingly, 77-89% of TLR7-NP vaccinated mice still developed high antibody titers against RBD variant from the Delta and Omicron lineages, while only 30-50% of TLR7-Alum vaccinated mice developed significantly lower antibody response against these variants.

Figures 8A, 8B, 8C, 8D:
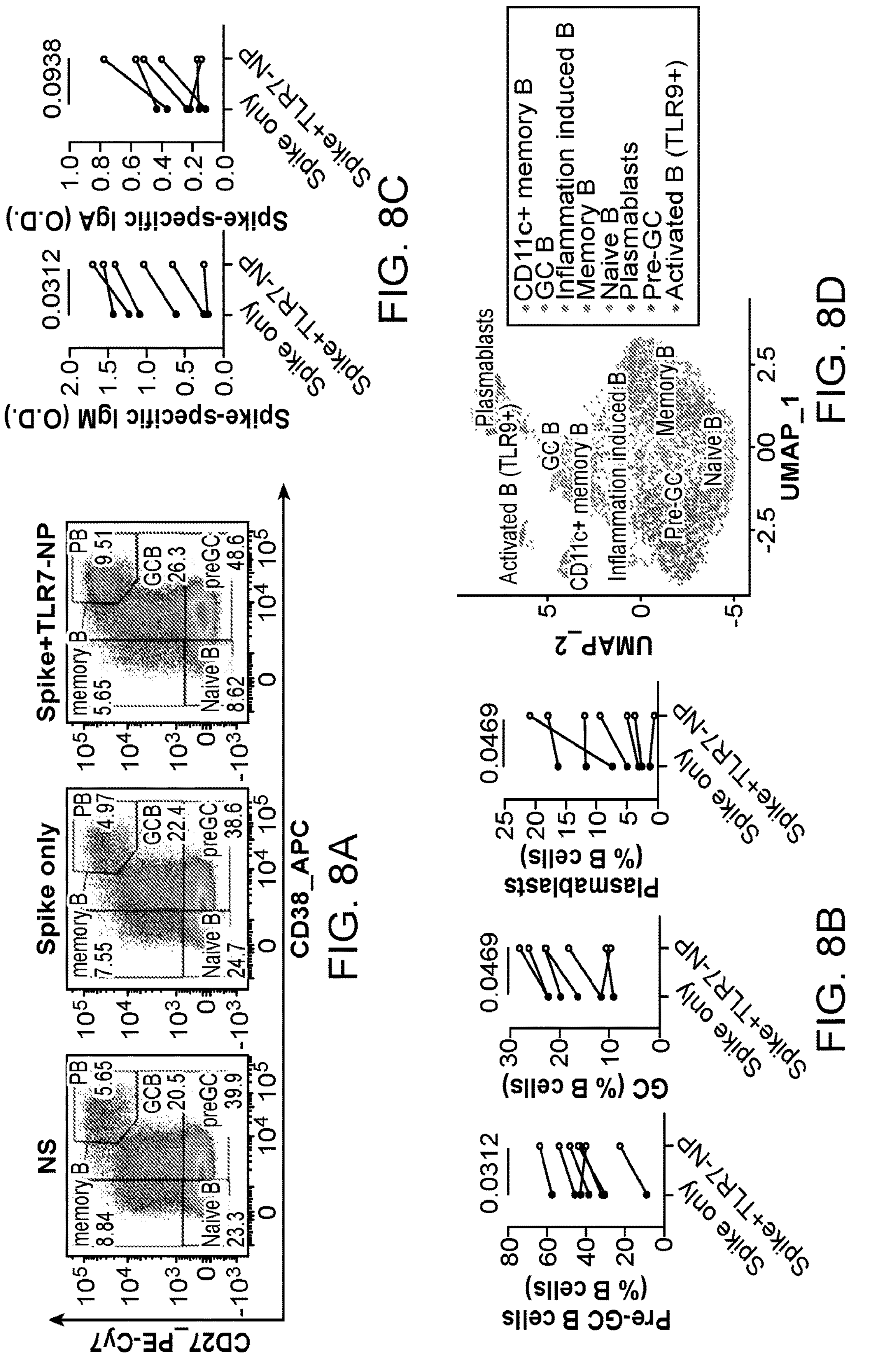
FIGS. 8A-8G. TLR7-NPs adjuvanted spike protein subunit vaccine elicits B cell differentiation and antibody response in human tonsil organoid cultures. (a) Representative flow cytometry staining of B cell phenotypes in unstimulated (NS), full-length spike protein only stimulated, and spike protein plus TLR7-NP stimulated organoid cultures from one donor on Day 14. Cells shown are pre-gated on total live B cells ($CD45^{+}CD19^{+}CD3^{-}$). (b) Quantification of B cell differentiation towards pre-GC ($CD38^{+}CD27^{-}$), GC ($CD38^{+}CD27^{+}$), and plasmablast ($CD38^{+}CD27^{++}$) in spike only stimulated, and spike plus TLR7-NPs stimulated organoid cultures (n=7 donors). (c) Quantification of spike-specific IgM and IgA from spike only stimulated and spike plus TLR7-NPs stimulated culture supernatants on Day 14 (n=6 donors). P values shown were calculated by Wilcoxon matched-pairs signed rank test. (d) UMAP projection of tonsillar B cell scRNA-seq clusters. (e) Quantification of B cell differentiation subclusters (both frequency and total cell number in organoids) in scRNA-seq. (f) Frequency quantification of plasmablast subclusters in scRNA-seq. (g) Gene ontologies for genes significantly upregulated in TLR7-NP plus antigen stimulated cultures versus antigen only stimulated cultures on day 4.

TLR7-NPs adjuvanted spike protein subunit vaccine elicits B cell differentiation and antibody response in 3D human tonsil organoid cultures. To further investigate the translational potential of TLR7-NPs as an adjuvant for both mouses and human analyses, we used our recently developed human tonsil organoid system to assess the effects of TLR7-NPs when combined with the full-length SARS-CoV-2 spike protein. Organoid cultures were prepared and stimulated with spike protein with or without TLR7-NPs. After 14 days in culture, we assessed the phenotype changes of B cells in the culture and antibody specificities against SARS-CoV-2 spike in the supernatants. As shown in FIG. 8*a* and FIG. 8*b*, we observed a significant increase in Pre-GC B cells, GC-B cells and plasmablast differentiation in a subset of donors upon stimulation of Spike with TLR7-NPs compared to Spike protein only controls. Spike-specific IgM and IgA antibodies increased in 5 out of 6 donors when stimulating with Spike+TLR7-NPs compared to Spike alone (FIG. 8*c*). In addition, we also tested the adjuvanticity of TLR7-NPs in combination with a subunit vaccine currently under clinical testing, comprised of the SARS-CoV-2 spike protein RBD displayed on a 153-50 protein nanoparticle scaffold (termed as RBD-NP) in this organoid system.

Figure 8E:
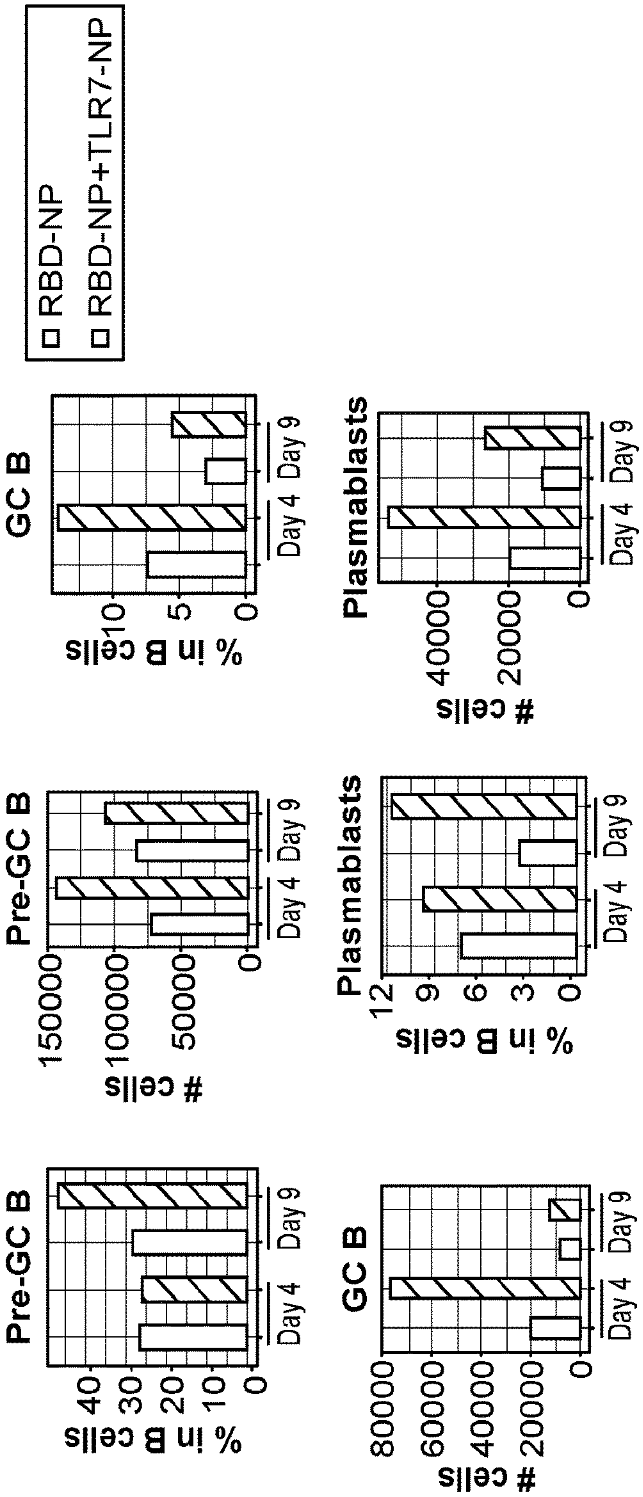
Figure 8F:
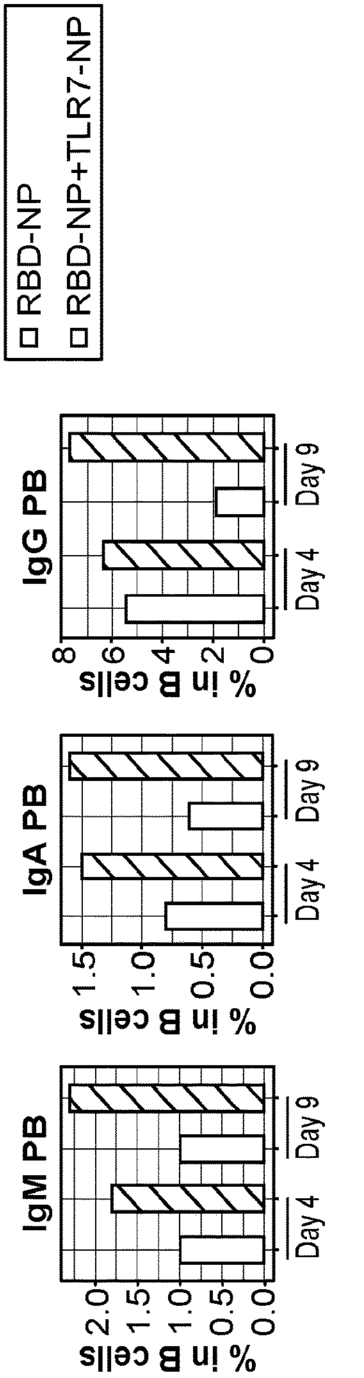

We performed a time-course single-cell RNA sequencing (scRNA-seq) study using the BD Rhapsody platform for sorted B cells from unadjuvanted RBD-NP cultures and RBD-NP+TLR7-NPs stimulated tonsil organoid cultures. We first examined B cells states within our single-cell transcriptomic atlas and identified 8 distinct B cell populations by uniform manifold approximation and projection (UMAP) based on their gene expression profile (FIG. 8*d*). As shown in FIG. 8*e*, both the frequencies and the numbers of GC B and plasmablasts (PB) notably increased as early as 4 days' post stimulation with the RBD-NP plus TLR7-NPs compared to RBD-NP alone. This is well in line with our previous observation that TLR7-NPs induced the early promotion of both extrafollicular responses and GC responses in the mouse. More importantly, IgM PB, IgA PB, and IgG PB were all significantly increased in RBD-NP plus TLR7-NPs stimulated cultures, indicating the broad effects of TLR7-NPs on the antibody isotype switching of B cells in human tonsil organoids (FIG. 8*f*).

Figure 8G:
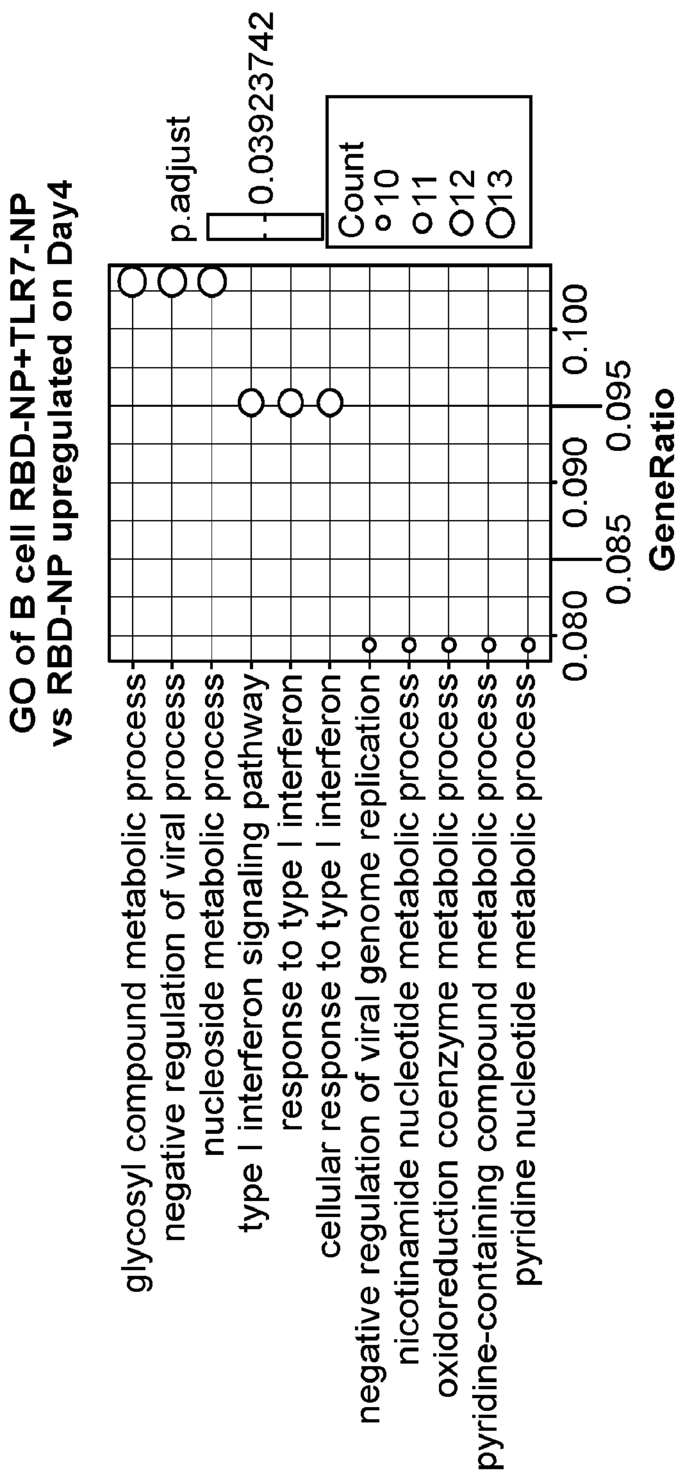

To further understand TLR7-NP-mediated signaling pathways on B cell differentiation, we then compared gene expression within B cells in both RBD-NP alone stimulated- and RBD-NP+TLR7-NPs stimulated cultures. Gene Ontology (GO) analysis showed that genes associated with responses to viruses and type 1 interferon are remarkedly upregulated on 4-day-old tonsil cultures stimulated with RBD-NP plus TLR7-NPs compared to RBD-NP alone (FIG. 8*g*).

Figure 9A:
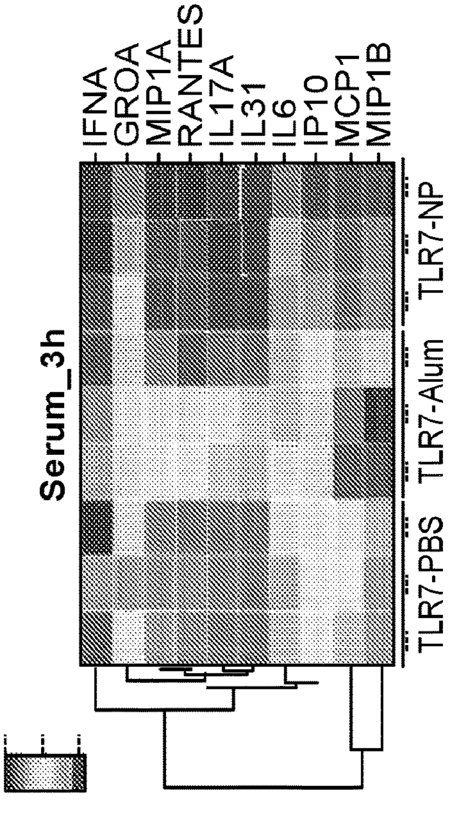
FIGS. 9A-9B. TLR7-NPs adjuvant minimizes systemic immune toxicity. (a) The expression of top-10 elevated cytokines in the serum of C57BL/6 mice 3 hours after a single immunization of NP-OVA protein (50 μg) plus TLR7 agonist (20 μg) in three different platforms (PBS, Alum, or NPs). (b) The clinical chemistry of immunized mice at Day 1, Day 4 and Day 7 post immunization.
Figure 9B:
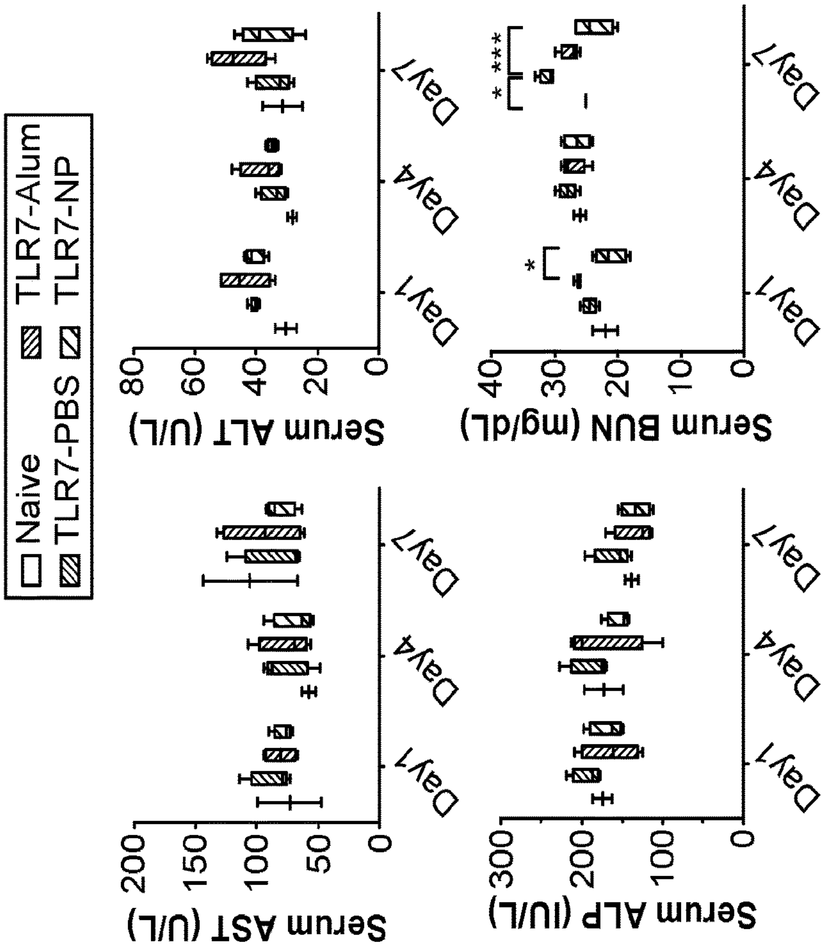

TLR7-NPs adjuvant minimizes systemic immune toxicity. As targets for the large healthy population, the safety profile of vaccine adjuvant couldn't be emphasized enough. We next evaluated systemic toxicity by intramuscularly injecting the TLR7-NPs adjuvanted vaccine into C57BL/6 mice. TLR7(PBS) and TLR7 (Alum) were used as controls. Both TLR7 (PBS) and TLR7 (Alum) rapidly diffused into circulation within 3 hours after a single injection, leading to acute inflammation, characterized by multiple elevated serum inflammatory cytokines including IL-6, IP-10, MCP-1, and MIP1B (FIG. 9*a*). We further evaluated the long-term toxicity by clinical chemistry at day 1, day 4, and day 7 post immunization. The result showed the significantly increased blood urea nitrogen (BUN) enzyme level in both TLR7 (PBS) and TLR7(Alum) immunized groups, indicating the kidney toxicities, presumably caused by fast renal clearance of small molecular TLR7 agonist in these two formulations (FIG. 9*b*). In contrast, TLR7-NPs adjuvanted vaccines showed negligible systemic inflammation and chronic renal toxicity.

Figure 10:
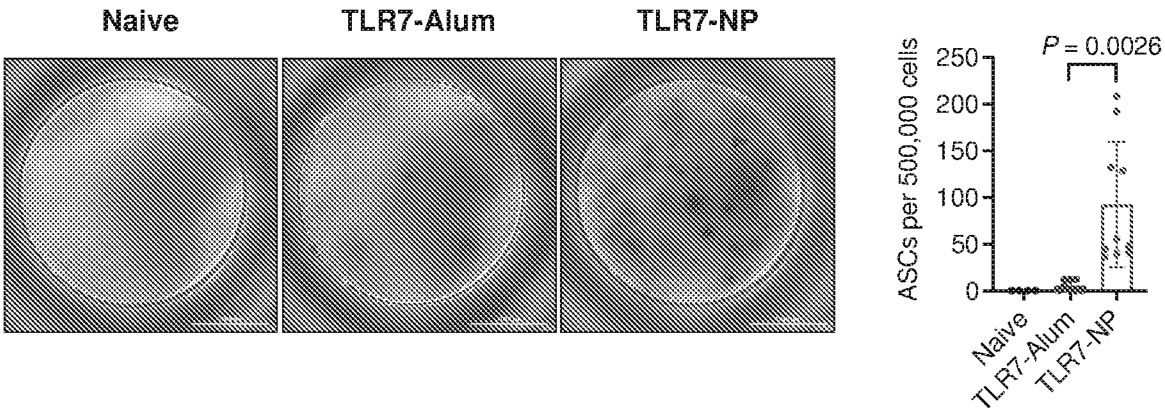
FIG. 10. TLR7-NP adjuvanted spike vaccine in comparison with TLR7-Alum adjuvanted spike vaccine induces significantly higher spike-specific antibody-secreting cells (ASCs) in the bone marrow. Scanned ELISPOT plate images of ASCs at one-year post immunization assayed in bone marrow aspirate are shown (Left). Quantification of the frequencies of IgG-secreting Spike-specific ASCs in bone marrow aspirates (Right). Data are analyzed by unpaired t test with Welch's correction. P values are as shown.

TLR7-NPs adjuvanted spike immunization induces durable antibody responses. To assess the longevity of antibody responses induced by TLR7-NP or TLR7-Alum adjuvanted spike vaccination, we performed an ELISPOT assay of bone marrow plasma cells one year after immunization with TLR7-NPs and SARS-CoV-2 spike protein. The results showed significantly increased SARS-CoV-2 spike-specific plasma cells in the bone marrow elicited by vaccination with TLR7-NP compared to control TLR7-Alum (FIG. 10).

In this invention, we developed a clinically translatable TLR7-NPs based adjuvant system to enhance the vaccine-induced immune response without causing undesirable systemic inflammation. Most importantly, the developed TLR7-NP holds a great promise to design and develop broadly protective or universal influenza virus vaccines, which would abolish the need for annual reformation and re-administration of seasonal vaccines. Not limited to the influenza vaccine, TLR7-NP also holds great potential for developing future universal coronavirus vaccine to markedly increase our pandemic preparedness.

What is claimed is:

1. A vaccine composition comprising:

a pathogen antigen; and a plurality of nanoparticles, wherein each nanoparticle comprises:

(i) an adjuvant-polymer conjugate comprising a toll-like receptor 7 (TLR7) agonist conjugated via an ester linkage to a poly(lactic acid), wherein the TLR7 agonist is selected from the group consisting of resiquimod and gardiquimod; and (ii) a copolymer selected from the group consisting of a poly(ethylene glycol)-b-poly(lactic-co-glycolic acid), a poly(ethylene glycol)-b-poly(lactic acid), and a poly (ethylene glycol)-b-poly(glycolic acid); and (iii) wherein the nanoparticle is formed by co-precipitation of (i) and (ii).

2. The vaccine composition of claim 1, wherein the TLR7 agonist is gardiquimod.

3. The vaccine composition of claim 1, wherein the copolymer is poly(ethylene glycol)-b-poly(lactic-co-glycolic acid).

4. The vaccine composition of claim 2, wherein the copolymer is poly(ethylene glycol)-b-poly(lactic-co-glycolic acid).

5. The vaccine composition of claim 1, wherein the nanoparticles are from about 60 nm to about 85 nm in diameter.

6. The vaccine composition of claim 1, wherein the standard deviation of diameter of the nanoparticles is less than about 15 nm.

7. The vaccine composition of claim 1, wherein the pathogen antigen is a polypeptide.

8. The vaccine composition of claim 1, wherein the pathogen antigen is a virus protein subunit.

9. The vaccine composition of claim 1, wherein the pathogen antigen is an inactivated whole virus.

10. The vaccine composition of claim 1, wherein the pathogen antigen is a coronaviral or influenza antigen.

11. The vaccine composition of claim 1, wherein the pathogen antigen is a SARS-CoV-2 antigen.

12. The vaccine composition of claim 1, wherein the plurality of nanoparticles comprises the pathogen antigen, which is co-precipitated with (i) the adjuvant-polymer conjugate and (ii) the copolymer.

13. The vaccine composition of claim 1, wherein the pathogen antigen is conjugated to the nanoparticles.

14. The vaccine composition of claim 1, wherein the pathogen antigen is not conjugated to the nanoparticles.

15. The vaccine composition of claim 2, wherein the adjuvant-polymer conjugate has the following structure:

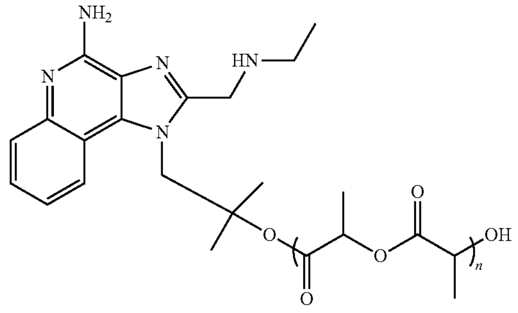

where n is from 5 to 100.

16. A method of inducing an antigen-specific immune response in a mammal in need thereof comprising intramuscularly, subcutaneously, or intranasally administering to the mammal an effective amount of the vaccine composition of claim 1.

17. A method of inducing an antigen-specific immune response in a mammal in need thereof comprising intramuscularly, subcutaneously, or intranasally administering to the mammal an effective amount of the vaccine composition of claim 15.

* * * * *